US011224782B2

(12) United States Patent
Blahnik et al.

(10) Patent No.: US 11,224,782 B2
(45) Date of Patent: Jan. 18, 2022

(54) PHYSICAL ACTIVITY MONITORING AND MOTIVATING WITH AN ELECTRONIC DEVICE

(71) Applicant: Apple Inc., Cupertino, CA (US)

(72) Inventors: Jay K. Blahnik, San Francisco, CA (US); Aled H. Williams, San Francisco, CA (US); Anthony D'Auria, San Francisco, CA (US); David S. Clark, San Jose, CA (US); Keith P. Avery, Sunnyvale, CA (US); Eamon F. Gilravi, San Francisco, CA (US); Molly P. Wiebe, San Francisco, CA (US); Julie A. Arney, Los Gatos, CA (US)

(73) Assignee: Apple Inc., Cupertino, CA (US)

( * ) Notice: Subject to any disclaimer, the term of this patent is extended or adjusted under 35 U.S.C. 154(b) by 386 days.

(21) Appl. No.: 15/888,728

(22) Filed: Feb. 5, 2018

(65) Prior Publication Data

US 2018/0345078 A1 Dec. 6, 2018

Related U.S. Application Data

(60) Provisional application No. 62/514,893, filed on Jun. 4, 2017.

(51) Int. Cl.
| | |
|---|---|
| *A63B 24/00* | (2006.01) |
| *G06Q 50/22* | (2018.01) |
| *A61B 5/11* | (2006.01) |
| *A61B 5/00* | (2006.01) |
| *A61B 5/024* | (2006.01) |
| *A61B 5/021* | (2006.01) |

(52) U.S. Cl.
CPC ........ *A63B 24/0062* (2013.01); *A61B 5/1118* (2013.01); *A61B 5/742* (2013.01); *G06Q 50/22* (2013.01); *A61B 5/021* (2013.01); *A61B 5/024* (2013.01); *A61B 5/02416* (2013.01); *A61B 5/681* (2013.01); *A61B 2503/10* (2013.01); *A61B 2562/0219* (2013.01)

(58) Field of Classification Search
None
See application file for complete search history.

(56) References Cited

U.S. PATENT DOCUMENTS 5,387,164 A * 2/1995 Brown, Jr. .............. G06F 15/02
482/9
7,662,065 B1 * 2/2010 Kahn ..................... G16H 20/30
482/9

(Continued)

FOREIGN PATENT DOCUMENTS

| CN | 102314557 A | 1/2012 |
| CN | 103154954 A | 6/2013 |

OTHER PUBLICATIONS

"First Office Action," dated Oct. 28, 2020 in Chinese Application No. 201880037006.2. 16 pages, includes English translation.

(Continued)

*Primary Examiner* — William D Ermlick
(74) *Attorney, Agent, or Firm* — Kilpatrick Townsend & Stockton

(57) ABSTRACT

Systems, methods, and computer-readable media for monitoring and motivating physical activity of a user with an electronic device are provided.

21 Claims, 12 Drawing Sheets

(56) References Cited

U.S. PATENT DOCUMENTS

| | | | | |
|---|---|---|---|---|
| 8,690,578 | B1* | 4/2014 | Nusbaum | G16H 20/30 434/127 |
| 9,460,632 | B2* | 10/2016 | Watterson | A61B 5/0022 |
| 9,881,511 | B1* | 1/2018 | Srinivasan | G16H 50/20 |
| 10,471,302 | B1* | 11/2019 | Ehlert | A61B 5/4866 |
| 2006/0217231 | A1* | 9/2006 | Parks | A63B 69/0028 482/3 |
| 2007/0072156 | A1* | 3/2007 | Kaufman | G16H 20/60 434/236 |
| 2009/0105047 | A1* | 4/2009 | Guidi | A61B 5/0002 482/9 |
| 2011/0021953 | A1* | 1/2011 | Sanematsu | A63B 24/0062 601/5 |
| 2011/0098928 | A1* | 4/2011 | Hoffman | A63B 71/0622 702/5 |
| 2011/0281248 | A1* | 11/2011 | Feenstra | G09B 19/003 434/247 |
| 2012/0171649 | A1* | 7/2012 | Wander | G06F 19/3481 434/247 |
| 2012/0301856 | A1* | 11/2012 | Quatrochi | A63B 24/0075 434/247 |
| 2013/0303335 | A1* | 11/2013 | Guidi | A61B 5/0002 482/9 |
| 2014/0052280 | A1* | 2/2014 | Yuen | G06F 11/00 700/91 |
| 2014/0067494 | A1* | 3/2014 | Squires | G09B 19/0038 705/14.1 |
| 2014/0200691 | A1* | 7/2014 | Lee | A61B 5/1118 700/91 |
| 2014/0244009 | A1* | 8/2014 | Mestas | A63B 24/0062 700/91 |
| 2014/0272845 | A1 | 9/2014 | Hendriks et al. | |
| 2014/0276244 | A1* | 9/2014 | Kamyar | A61B 5/7435 600/595 |
| 2014/0337451 | A1* | 11/2014 | Choudhary | A61B 5/22 709/206 |
| 2014/0363804 | A1* | 12/2014 | Vercelli | G09B 19/00 434/408 |
| 2015/0104759 | A1* | 4/2015 | Block | G09B 19/0092 434/127 |
| 2015/0130830 | A1* | 5/2015 | Nagasaki | A61B 5/7435 345/592 |
| 2015/0269848 | A1* | 9/2015 | Yuen | G09B 19/00 434/236 |
| 2015/0339949 | A1 | 11/2015 | Landers | |
| 2016/0058337 | A1* | 3/2016 | Blahnik | A61B 5/1112 600/595 |
| 2016/0089569 | A1* | 3/2016 | Blahnik | G16H 20/30 434/247 |
| 2016/0189566 | A1* | 6/2016 | Rot | A61B 5/4803 434/185 |
| 2016/0217266 | A1* | 7/2016 | Damani | G06F 19/3418 |
| 2016/0261528 | A1* | 9/2016 | Blahnik | G06F 19/3481 |
| 2016/0317867 | A1* | 11/2016 | Hoffman | G06Q 50/01 |
| 2016/0321935 | A1* | 11/2016 | Mohler | G09B 5/08 |
| 2016/0346607 | A1* | 12/2016 | Rapfogel | A61B 5/4866 |
| 2016/0358506 | A1* | 12/2016 | Bahouth | G09B 19/0092 |
| 2017/0239523 | A1* | 8/2017 | Cheng | A61B 5/1118 |
| 2017/0301257 | A1* | 10/2017 | Laing | A61B 5/6898 |
| 2017/0308677 | A1* | 10/2017 | Shibuya | A61B 5/11 |
| 2017/0358242 | A1* | 12/2017 | Thompson | G16H 40/63 |
| 2018/0056130 | A1* | 3/2018 | Bitran | A63B 71/0622 |
| 2018/0174685 | A1* | 6/2018 | Hamalainen | A61B 5/0205 |
| 2018/0178063 | A1* | 6/2018 | Silver | G16H 50/30 |
| 2018/0207483 | A1* | 7/2018 | Mestas | A63B 24/0062 |
| 2018/0277013 | A1* | 9/2018 | Van Halteren | G09B 19/00 |
| 2018/0293911 | A1* | 10/2018 | Rastegar-Panah | G16H 50/20 |
| 2018/0345078 | A1* | 12/2018 | Blahnik | A61B 5/742 |
| 2018/0345081 | A1* | 12/2018 | Lee | G06Q 50/22 |
| 2019/0122523 | A1* | 4/2019 | Roberts | A61B 5/1118 |
| 2019/0358493 | A1* | 11/2019 | Quatrochi | A63B 71/0622 |

OTHER PUBLICATIONS

"Notification of Second Office Action," dated May 26, 2021 in Chinese Patent Application No. 201880037006.2. 14 pages (includes English translation).

"Rejection Decision (PCT Application in the National Phase," dated Nov. 11, 2021 in Chinese Patent Application No. 201880037006.2. 20 pages (includes English translation).

* cited by examiner

300

| State 1 | State 2 | State 3 | State 4 | State 5 | State 6 | State 7 | State 8 | State 9 | State 10 |
|---|---|---|---|---|---|---|---|---|---|
| IF: | IF: | IF: | IF: | IF: | IF: | IF: | IF: | IF: | IF: |
| B perfect | B not perfect | B not perfect | B not perfect | B not perfect | B not perfect | B not perfect | B not perfect | B not perfect | B not perfect |
|  | B ∨ ∅ | B ≠ ∅ | B ≠ ∅ | B ≠ ∅ | B ≠ ∅ | B ≠ ∅ | B ≠ ∅ | B ≠ ∅ | B ≠ ∅ |
|  |  | B < A*α% | B ≤ A*α% | B ∨ A*β% | B ≤ A*δ% | B = A | B ∨ A | B ∨ A*λ% | B ∧ Record*ω% |
|  |  |  | B ∧ A*β% | B ∧ A*δ% | B ∧ A | | B ≤ A*λ% | B ∧ A*ψ% | |
| THEN: | THEN: | THEN: | THEN: | THEN: | THEN: | THEN: | THEN: | THEN: | THEN: |
| Do Not Use | C=B+1 | Do Not Use | C=B | C=B*ε% | C=B*ζ% | C=B+1 | C=(A+B)/2 | C=B*ς% | C=Record+1 |

PHYSICAL ACTIVITY MONITORING AND MOTIVATING WITH AN ELECTRONIC DEVICE

CROSS-REFERENCE TO RELATED APPLICATION(S)

This application claims the benefit of prior filed U.S. Provisional Patent Application No. 62/514,893, filed Jun. 4, 2017, which is hereby incorporated by reference herein in its entirety.

TECHNICAL FIELD

This disclosure relates to monitoring a user's physical activity and motivating future physical activity with an electronic device.

BACKGROUND OF THE DISCLOSURE

A portable electronic device (e.g., a cellular telephone) may be provided with one or more sensing components (e.g., accelerometers, gyroscopes, etc.) that may be utilized for determining a physical activity of a user of the electronic device (e.g., distance traveled, Calories burned, etc.) over a period of time. Often, however, such determined physical activity data is not used to motivate a user to conduct relevant physical activity in the future.

SUMMARY OF THE DISCLOSURE

This document describes systems, methods, and computer-readable media for monitoring a user's physical activity and motivating future physical activity with an electronic device.

For example, a method of operating an electronic device to motivate a user may include, during each calendar sub-interval of a first calendar interval, detecting, with the electronic device, calendar sub-interval user fitness data, for each calendar sub-interval of the first calendar interval, determining whether the detected calendar sub-interval user fitness data satisfies a goal for that calendar sub-interval of the first calendar interval, determining the number of calendar sub-intervals of the first calendar interval for which the detected calendar sub-interval user fitness data satisfied the goal, defining a customized user challenge based on the determined number of calendar sub-intervals of the first calendar interval, and, at the beginning of a second calendar interval following the first calendar interval, presenting, with the electronic device, the customized user challenge.

As another example, a method of operating an electronic device to motivate a user may include, during each time sub-interval of a first time interval, detecting, with the electronic device, time sub-interval user activity data, for each time sub-interval of the first time interval, determining whether the detected time sub-interval user activity data satisfies a goal for that time sub-interval of the first time interval, during each time sub-interval of a second time interval that directly follows the first time interval, detecting, with the electronic device, time sub-interval user activity data, for each time sub-interval of the second time interval, determining whether the detected time sub-interval user activity data satisfies a goal for that time sub-interval of the second time interval, determining the number of time sub-intervals of the first time interval for which the detected time sub-interval user activity data satisfied the goal, determining the number of time sub-intervals of the second time interval for which the detected time sub-interval user activity data satisfied the goal, defining a customized user challenge based on at least one of the determined number of time sub-intervals of the first time interval and the determined number of time sub-intervals of the second time interval, at the beginning of a third time interval that directly follows the second time interval, presenting, with the electronic device, the customized user challenge.

As yet another example, a method of operating an electronic device to motivate a user may include, during each time sub-interval of a first time interval, detecting, with the electronic device, time sub-interval user activity data indicative of a time sub-interval user activity value for that time sub-interval of the first time interval, during each time sub-interval of a second time interval that directly follows the first time interval, detecting, with the electronic device, time sub-interval user activity data indicative of a time sub-interval user activity value for that time sub-interval of the second time interval, determining a first time interval user activity value based on the time sub-interval user activity values of the time sub-interval user activity data detected during the time sub-intervals of the first time interval, determining a second time interval user activity value based on the time sub-interval user activity values of the time sub-interval user activity data detected during the time sub-intervals of the second time interval, defining a customized user challenge based on each one of the first time interval user activity value and the second time interval user activity value, and, at the beginning of a third time interval that directly follows the second time interval, presenting, with the electronic device, the customized user challenge.

As yet another example, a method of operating an electronic device to motivate a user may include, during each time sub-interval of a first time interval, detecting, with the electronic device, time sub-interval user activity data, during each time sub-interval of a second time interval that directly follows the first time interval, detecting, with the electronic device, time sub-interval user activity data, selecting one user challenge type from a plurality of user challenge types, identifying, for the selected user challenge type, a first time interval user activity value based on the time sub-interval user activity data detected during the time sub-intervals of the first time interval, identifying, for the selected user challenge type, a second time interval user activity value based on the time sub-interval user activity data detected during the time sub-intervals of the second time interval, comparing the first time interval user activity value for the selected user challenge type to the second time interval user activity value for the selected user challenge type, defining a customized user challenge, for the selected user challenge type, based on the comparing, and, at the beginning of a third time interval that directly follows the second time interval, presenting, with the electronic device, the customized user challenge.

As yet another example, a method of operating an electronic device to motivate a user may include, during each time sub-interval of a first time interval, detecting, with the electronic device, time sub-interval user activity data, during each time sub-interval of a second time interval that directly follows the first time interval, detecting, with the electronic device, time sub-interval user activity data, identifying a first time interval user activity value based on the time sub-interval user activity data detected during the time sub-intervals of the first time interval, identifying a second time interval user activity value based on the time sub-interval user activity data detected during the time sub-intervals of the second time interval, defining a customized user challenge based on the first time interval user activity value and the second time interval user activity value, and, at the beginning of a third time interval that directly follows the second time interval, presenting, with the electronic device, the customized user challenge, wherein at least two of the following are true: (i) when the second time interval user activity value is within a first range of threshold percentages of the first time interval user activity value, the defining comprises defining the customized user challenge to challenge the user to generate, during the third time interval, third time interval user activity data indicative of a third time interval user activity value that is equal to a first threshold percentage of the second time interval user activity value; (ii) when the second time interval user activity value is within a second range of threshold percentages of the first time interval user activity value, the defining comprises defining the customized user challenge to challenge the user to generate, during the third time interval, third time interval user activity data indicative of a third time interval user activity value that is equal to the whole number that is closest to a second threshold percentage of the second time interval user activity value; (iii) when the second time interval user activity value is within a third range of threshold percentages of the first time interval user activity value, the defining comprises defining the customized user challenge to challenge the user to generate, during the third time interval, third time interval user activity data indicative of a third time interval user activity value that is equal to the whole number that is closest to a third threshold percentage of the second time interval user activity value; (iv) when the second time interval user activity value is equal to the first time interval user activity value, the defining comprises defining the customized user challenge to challenge the user to generate, during the third time interval, third time interval user activity data indicative of a third time interval user activity value that is greater than the second time interval user activity value by 1; (v) when the second time interval user activity value is within a fourth range of threshold percentages of the first time interval user activity value, the defining comprises defining the customized user challenge to challenge the user to generate, during the third time interval, third time interval user activity data indicative of a third time interval user activity value that is equal to the whole number that is closest to the average of the first time interval user activity value and the second time interval user activity value; and (vi) when the second time interval user activity value is within a fifth range of threshold percentages of the first time interval user activity value, the defining comprises defining the customized user challenge to challenge the user to generate, during the third time interval, third time interval user activity data indicative of a third time interval user activity value that is equal to the whole number that is closest to the third threshold percentage of the second time interval user activity value.

This Summary is provided only to summarize some example embodiments, so as to provide a basic understanding of some aspects of the subject matter described in this document. Accordingly, it will be appreciated that the features described in this Summary are only examples and should not be construed to narrow the scope or spirit of the subject matter described herein in any way. Unless otherwise stated, features described in the context of one example may be combined or used with features described in the context of one or more other examples. Other features, aspects, and advantages of the subject matter described herein will become apparent from the following Detailed Description, Figures, and Claims.

BRIEF DESCRIPTION OF THE DRAWINGS

The discussion below makes reference to the following drawings, in which like reference characters may refer to like parts throughout, and in which:

FIG. 9 illustrates a table for defining a challenge according to various examples.

DETAILED DESCRIPTION OF THE DISCLOSURE

Systems, methods, and computer-readable media may be provided to monitor and motivate with an electronic device a user's physical activity. Previously monitored physical activity of a user during one or more previous time intervals (e.g., as detected using one or more sensors (e.g., motion sensors, biometric sensors, etc.) may be analyzed based on one or more possible challenge types in order to define at least one challenge for an upcoming time interval. Different challenge types may be used for different types of user activity values that may be determined from detected user physical activity data, such as average number of a particular activity accomplishment per time sub-interval of the time interval, total number of a particular activity accomplishment (e.g., Calories burned, exercise time, distance traveled, workouts completed, etc.) for the time interval, number of time sub-intervals of the time interval for which a goal is satisfied by the user's physical activity, and/or the like. The appropriate user activity values from user physical activity data detected during one or more previous time intervals may be applied to one or more states of an appropriate challenge type to define a particular challenge for that particular challenge type. One or more challenges defined by one or more challenge types may then be analyzed to determine at least one particular challenge to present to a user. Each challenge may be operative to motivate a user to beat or repeat in an upcoming time interval the user activity value of a particular type as identified from the user's physical activity data detected during a previous time interval. This may enable challenges to be presented to a user that are customized to the user based on previous user achievements.

Figure 1:
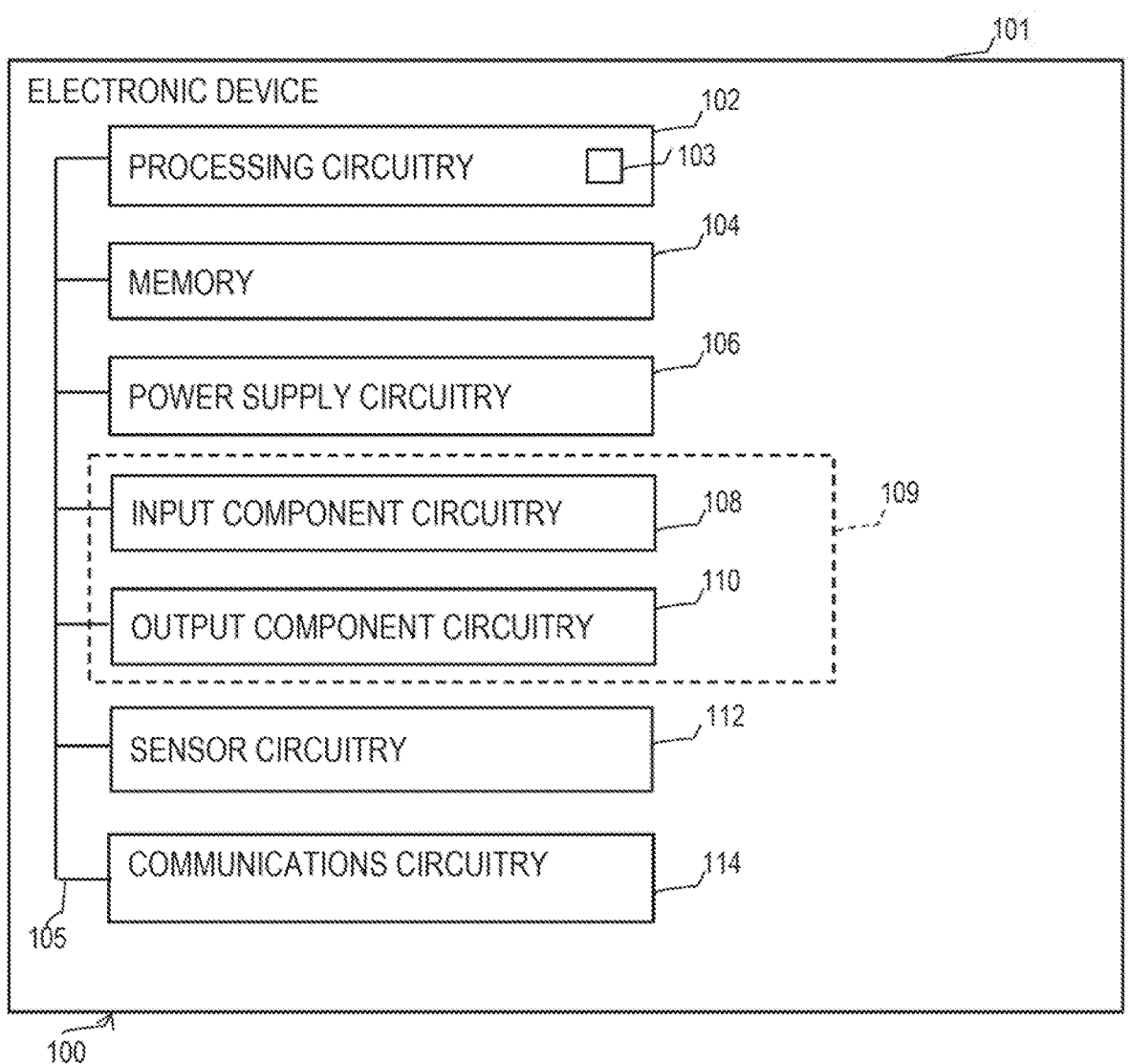
FIG. 1 is a schematic view of an illustrative electronic device for monitoring and motivating physical activity.

FIG. 1 is a schematic view of an illustrative electronic device 100 for monitoring and motivating a user's physical activity in accordance with some embodiments. Electronic device 100 can include, but is not limited to, a media player (e.g., an iPod™ available by Apple Inc. of Cupertino, Calif.), video player, still image player, game player, other media player, music recorder, movie or video camera or recorder, still camera, other media recorder, radio, medical equipment, domestic appliance, transportation vehicle instrument, musical instrument, calculator, cellular telephone (e.g., an iPhone™ available by Apple Inc.), other wireless communication device, personal digital assistant, remote control, pager, computer (e.g., a desktop, laptop, tablet (e.g., an iPad™ available by Apple Inc.), server, etc.), monitor, television, stereo equipment, set up box, set-top box, boom box, modem, router, printer, watch, biometric monitor, or any combination thereof. In some embodiments, electronic device 100 may perform a single function (e.g., a device dedicated to monitoring and motivating a user's physical activity) and, in other embodiments, electronic device 100 may perform multiple functions (e.g., a device that monitors and motivates a user's physical activity, plays music, and receives and transmits telephone calls).

Electronic device 100 may be any portable, mobile, hand-held, or miniature electronic device that may be configured to monitor and motivate a user's physical activity wherever a user travels. Some miniature electronic devices may have a form factor that is smaller than that of hand-held electronic devices, such as an iPod™. Illustrative miniature electronic devices can be integrated into various objects that may include, but are not limited to, watches (e.g., an Apple Watch™ available by Apple Inc.), rings, necklaces, belts, accessories for belts, headsets, accessories for shoes, virtual reality devices, glasses, other wearable electronics, accessories for sporting equipment, accessories for fitness equipment, key chains, or any combination thereof. Alternatively, electronic device 100 may not be portable at all, but may instead be generally stationary.

As shown in FIG. 1, for example, electronic device 100 may include processing circuitry 102, memory 104, power supply circuitry 106, input component circuitry 108, output component circuitry 110, sensor circuitry 112, and communications circuitry 114. Electronic device 100 may also include a bus 105 that may provide one or more wired or wireless communication links or paths for transferring data and/or power to, from, or between various other components of device 100. In some embodiments, one or more components of electronic device 100 may be combined or omitted. Moreover, electronic device 100 may include any other suitable components not combined or included in FIG. 1 and/or several instances of the components shown in FIG. 1. For the sake of simplicity, only one of each of the components is shown in FIG. 1.

Memory 104 may include one or more storage mediums, including, for example, a hard-drive, flash memory, permanent memory such as read-only memory ("ROM"), semi-permanent memory such as random access memory ("RAM"), any other suitable type of storage component, or any combination thereof. Memory 104 may include cache memory, which may be one or more different types of memory used for temporarily storing data for electronic device applications. Memory 104 may be fixedly embedded within electronic device 100 or may be incorporated onto one or more suitable types of cards that may be repeatedly inserted into and removed from electronic device 100 (e.g., a subscriber identity module ("SIM") card or secure digital ("SD") memory card). Memory 104 may store media data (e.g., music and image files), software (e.g., for implementing functions on device 100), firmware, preference information (e.g., media playback preferences), lifestyle information (e.g., food preferences), exercise information (e.g., information obtained by exercise monitoring equipment or any suitable sensor circuitry), transaction information (e.g., information such as credit card information), wireless connection information (e.g., information that may enable device 100 to establish a wireless connection), subscription information (e.g., information that keeps track of podcasts or television shows or other media a user subscribes to), contact information (e.g., telephone numbers and e-mail addresses), calendar information, pass information (e.g., transportation boarding passes, event tickets, coupons, store cards, financial payment cards, etc.), any other suitable data, or any combination thereof.

Power supply circuitry 106 can include any suitable circuitry for receiving and/or generating power, and for providing such power to one or more of the other components of electronic device 100. For example, power supply circuitry 106 can be coupled to a power grid (e.g., when device 100 is not acting as a portable device or when a battery of the device is being charged at an electrical outlet with power generated by an electrical power plant). As another example, power supply circuitry 106 can be configured to generate power from a natural source (e.g., solar power using solar cells). As another example, power supply circuitry 106 can include one or more batteries for providing power (e.g., when device 100 is acting as a portable device). For example, power supply circuitry 106 can include one or more of a battery (e.g., a gel, nickel metal hydride, nickel cadmium, nickel hydrogen, lead acid, or lithium-ion battery), an uninterruptible or continuous power supply ("UPS" or "CPS"), and circuitry for processing power received from a power generation source (e.g., power generated by an electrical power plant and delivered to the user via an electrical socket or otherwise). The power can be provided by power supply circuitry 106 as alternating current or direct current, and may be processed to transform power or limit received power to particular characteristics. For example, the power can be transformed to or from direct current, and constrained to one or more values of average power, effective power, peak power, energy per pulse, voltage, current (e.g., measured in amperes), or any other characteristic of received power. Power supply circuitry 106 can be operative to request or provide particular amounts of power at different times, for example, based on the needs or requirements of electronic device 100 or periphery devices that may be coupled to electronic device 100 (e.g., to request more power when charging a battery than when the battery is already charged).

One or more input components 108 may be provided to permit a user to interact or interface with device 100. For example, input component circuitry 108 can take a variety of forms, including, but not limited to, a touch pad, dial, click wheel, scroll wheel, touch screen, one or more buttons (e.g., a keyboard), mouse, joy stick, track ball, microphone, camera, scanner (e.g., a bar code scanner or any other suitable scanner that may obtain product identifying information from a code, such as a bar code, or the like), proximity sensor, light detector, biometric sensor (e.g., a fingerprint reader or other feature recognition sensor, which may operate in conjunction with a feature-processing application that may be accessible to electronic device 100 for authenticating a user), line-in connector for data and/or power, and combinations thereof. Each input component 108 can be configured to provide one or more dedicated control functions for making selections or issuing commands associated with operating device 100.

Electronic device 100 may also include one or more output components 110 that may present information (e.g., graphical, audible, and/or tactile information) to a user of device 100. For example, output component circuitry 110 of electronic device 100 may take various forms, including, but not limited to, audio speakers, headphones, line-out connectors for data and/or power, visual displays, infrared ports, tactile/haptic outputs (e.g., rumblers, vibrators, etc.), and combinations thereof. As a particular example, electronic device 100 may include a display output component as output component 110, where such a display output component may include any suitable type of display or interface for presenting visual data to a user. A display output component may include a display embedded in device 100 or coupled to device 100 (e.g., a removable display). A display output component may include, for example, a liquid crystal display ("LCD"), a light emitting diode ("LED") display, an organic light-emitting diode ("OLED") display, a surface-conduction electron-emitter display ("SED"), a carbon nanotube display, a nanocrystal display, any other suitable type of display, or combination thereof. Alternatively, a display output component can include a movable display or a projecting system for providing a display of content on a surface remote from electronic device 100, such as, for example, a video projector, a head-up display, or a three-dimensional (e.g., holographic) display. As another example, a display output component may include a digital or mechanical viewfinder, such as a viewfinder of the type found in compact digital cameras, reflex cameras, or any other suitable still or video camera. A display output component may include display driver circuitry, circuitry for driving display drivers, or both, and such a display output component can be operative to display content (e.g., media playback information, application screens for applications implemented on electronic device 100, information regarding ongoing communications operations, information regarding incoming communications requests, device operation screens, etc.) that may be under the direction of processor 102.

It should be noted that one or more input components and one or more output components may sometimes be referred to collectively herein as an input/output ("I/O") component or I/O circuitry or I/O interface (e.g., input component 108 and output component 110 as I/O component or I/O interface 109). For example, input component 108 and output component 110 may sometimes be a single I/O component 109, such as a touch screen, that may receive input information through a user's touch (e.g., multi-touch) of a display screen and that may also provide visual information to a user via that same display screen.

Sensor circuitry 112 may include any suitable sensor or any suitable combination of sensors operative to detect movements of electronic device 100 and/or any other characteristics of device 100 or its environment (e.g., physical activity or other characteristics of a user of device 100). For example, sensor circuitry 112 may include one or more three-axis acceleration motion sensors (e.g., an accelerometer) that may be operative to detect linear acceleration in three directions (i.e., the x- or left/right direction, the y- or up/down direction, and the z- or forward/backward direction). As another example, sensor circuitry 112 may include one or more single-axis or two-axis acceleration motion sensors that may be operative to detect linear acceleration only along each of the x- or left/right direction and the y- or up/down direction, or along any other pair of directions. In some embodiments, sensor circuitry 112 may include an electrostatic capacitance (e.g., capacitance-coupling) accelerometer that may be based on silicon micro-machined micro electro-mechanical systems ("MEMS") technology, including a heat-based MEMS type accelerometer, a piezoelectric type accelerometer, a piezo-resistance type accelerometer, and/or any other suitable accelerometer (e.g., which may provide a pedometer or other suitable function). In some embodiments, sensor circuitry 112 may be operative to directly or indirectly detect rotation, rotational movement, angular displacement, tilt, position, orientation, motion along a non-linear (e.g., arcuate) path, or any other non-linear motions. Additionally or alternatively, sensor circuitry 112 may include one or more angular rate, inertial, and/or gyro-motion sensors or gyroscopes for detecting rotational movement. For example, sensor circuitry 112 may include one or more rotating or vibrating elements, optical gyroscopes, vibrating gyroscopes, gas rate gyroscopes, ring gyroscopes, magnetometers (e.g., scalar or vector magnetometers), compasses, and/or the like. Any other suitable sensors may also or alternatively be provided by sensor circuitry 112 for detecting motion on device 100, such as any suitable pressure sensors, altimeters, or the like. Using sensor circuitry 112, electronic device 100 may be configured to determine a velocity, acceleration, orientation, and/or any other suitable motion attribute of electronic device 100.

Sensor circuitry 112 may include any suitable sensor(s), including, but not limited to, one or more of a GPS sensor, accelerometer, directional sensor (e.g., compass), gyroscope, motion sensor, pedometer, passive infrared sensor, ultrasonic sensor, microwave sensor, a tomographic motion detector, a camera, a biometric sensor, a light sensor, a timer, or the like. In some examples, a biometric sensor may include, but is not limited to, one or more health-related optical sensors, capacitive sensors, thermal sensors, electric field ("eField") sensors, and/or ultrasound sensors, such as photoplethysmogram ("PPG") sensors, electrocardiography ("ECG") sensors, galvanic skin response ("GSR") sensors, posture sensors, stress sensors, photoplethysmogram sensors, and/or the like. These sensors can generate data providing health-related information associated with the user. For example, PPG sensors can provide information regarding a user's respiratory rate, blood pressure, and/or oxygen saturation. ECG sensors can provide information regarding a user's heartbeats. GSR sensors can provide information regarding a user's skin moisture, which may be indicative of sweating and can prioritize a thermostat application to determine a user's body temperature. In some examples, each sensor can be a separate device, while, in other examples, any combination of two or more of the sensors can be included within a single device. For example, a gyroscope, accelerometer, photoplethysmogram, galvanic skin response sensor, and temperature sensor can be included within a wearable electronic device, such as a smart watch, while a scale, blood pressure cuff, blood glucose monitor, SpO2 sensor, respiration sensor, posture sensor, stress sensor, and asthma inhaler can each be separate devices. While specific examples are provided, it should be appreciated that other sensors can be used and other combinations of sensors can be combined into a single device. Using one or more of these sensors, device 100 can determine physiological characteristics of the user while performing a detected activity, such as a heart rate of a user associated with the detected activity, average body temperature of a user detected during the detected activity, any normal or abnormal physical conditions associated with the detected activity, or the like. In some examples, a GPS sensor or any other suitable location detection component(s) of device 100 can be used to determine a user's location and movement, as well as a displacement of the user's motion. An accelerometer, directional sensor, and/or gyroscope can further generate activity data that can be used to determine whether a user of device 100 is engaging in an activity, is inactive, or is performing a gesture. Device 100 can further include a timer that can be used, for example, to add time dimensions to various attributes of the detected physical activity, such as a duration of a user's physical activity or inactivity, time(s) of a day when the activity is detected or not detected, and/or the like. One or more sensors of sensor circuitry or component 112 may be embedded in a body (e.g., housing 101) of device 100, such as a long a bottom surface that may be operative to contact a user, or can be positioned at any other desirable location. In some examples, different sensors can be placed in different locations inside or on the surfaces of device 100 (e.g., some located inside housing 101) and some attached to an attachment mechanism (e.g., a mechanism 111 (e.g., a wrist band coupled to a housing of a wearable device)), or the like. In other examples, one or more sensors can be worn by a user separately from device 100. In such cases, the sensors can be configured to communicate with device 100 using a wired and/or wireless technology (e.g., via communications circuitry 114). In some examples, sensors can be configured to communicate with each other and/or share data collected from one or more sensors. In some other examples, device 100 can be waterproof such that the sensors can detect a user's activity in water.

Communications circuitry 114 may be provided to allow device 100 to communicate with one or more other electronic devices or servers using any suitable communications protocol. For example, communications circuitry 114 may support Wi-Fi™ (e.g., an 802.11 protocol), ZigBee™ (e.g., an 802.15.4 protocol), WiDi™, Ethernet, Bluetooth™, Bluetooth™ Low Energy ("BLE"), high frequency systems (e.g., 900 MHz, 2.4 GHz, and 5.6 GHz communication systems), infrared, transmission control protocol/internet protocol ("TCP/IP") (e.g., any of the protocols used in each of the TCP/IP layers), Stream Control Transmission Protocol ("SCTP"), Dynamic Host Configuration Protocol ("DHCP"), hypertext transfer protocol ("HTTP"), BitTorrent™, file transfer protocol ("FTP"), real-time transport protocol ("RTP"), real-time streaming protocol ("RTSP"), real-time control protocol ("RTCP"), Remote Audio Output Protocol ("RAOP"), Real Data Transport Protocol™ ("RDTP"), User Datagram Protocol ("UDP"), secure shell protocol ("SSH"), wireless distribution system ("WDS") bridging, any communications protocol that may be used by wireless and cellular telephones and personal e-mail devices (e.g., Global System for Mobile Communications ("GSM"), GSM plus Enhanced Data rates for GSM Evolution ("EDGE"), Code Division Multiple Access ("CDMA"), Orthogonal Frequency-Division Multiple Access ("OFDMA"), high speed packet access ("HSPA"), multi-band, etc.), any communications protocol that may be used by a low power Wireless Personal Area Network ("6LoW-PAN") module, Near Field Communication ("NFC"), any other communications protocol, or any combination thereof. Communications circuitry 114 may also include or be electrically coupled to any suitable transceiver circuitry that can enable device 100 to be communicatively coupled to another device (e.g., a host computer or an accessory device) and communicate with that other device wirelessly, or via a wired connection (e.g., using a connector port). Communications circuitry 114 may be configured to determine a geographical position of electronic device 100. For example, communications circuitry 114 may utilize the global positioning system ("GPS") or a regional or site-wide positioning system that may use cell tower positioning technology or Wi-Fi™ technology.

Processing circuitry 102 of electronic device 100 may include any processing circuitry that may be operative to control the operations and performance of one or more components of electronic device 100. For example, processor 102 may receive input signals from any input component 108 and/or sensor circuitry 112 and/or communications circuitry 114 and/or drive output signals through any output component 110 and/or communications circuitry 114. As shown in FIG. 1, processor 102 may be used to run one or more applications, such as an application 103. Application 103 may include, but is not limited to, one or more operating system applications, firmware applications, media playback applications, media editing applications, communications applications, pass applications, calendar applications, state determination applications, biometric feature-processing applications, activity monitoring applications, activity motivating applications, and/or any other suitable applications. For example, processor 102 may load application 103 as a user interface program to determine how instructions or data received via an input component 108 and/or any other component of device 100 may manipulate the one or more ways in which information may be stored and/or provided to the user via an output component 110 and/or any other component of device 100. Any application 103 may be accessed by any processing circuitry 102 from any suitable source, such as from memory 104 (e.g., via bus 105) or from another device or server (not shown) (e.g., via communications circuitry 114). Processor 102 may include a single processor or multiple processors. For example, processor 102 may include at least one "general purpose" microprocessor, a combination of general and special purpose microprocessors, instruction set processors, graphics processors, video processors, communications processors, motion processors, biometric processors, application processors, and/or related chips sets, and/or special purpose microprocessors. Processor 102 also may include on board memory for caching purposes.

Processor 102 may be configured to process any activity data sensed by sensor circuitry 112 to determine if the activity data represents a physical activity or a gesture being performed by a user, where a physical activity may generally refer to any bodily motion that can enhance or maintain physical fitness and overall health and wellness. Additionally, processor 102 can be configured to identify the type of physical activity represented by the activity data, such as whether the detected activity is standing, bicycling, jogging, walking, running, swimming, jumping, going up stairs, intense bodily movements, such as wrestling, or the like. Examples of gestures recognizable by device 100 may include, but are not limited to, waving hands, moving fingers, such as typing, or the like. In some examples, processor 102 may be operative to determine a physical activity of a user based on one or more physical activity recognition algorithms. Some algorithms (e.g., of any application 103) may be operative to instruct processor 102 to recognize movement of device 100 as being associated with a gesture if the detected movement does not have an intensity level greater than or equal to a physical activity threshold. The physical activity threshold can be represented as a distance traveled, a number of Calories burned, a number of steps taken, any one or more of these attributes calculated per unit time, or the like. The algorithms for storing such instructions for one or more processors 102 can be stored in memory 104.

Processor 102 may be operative to determine, based on the physical activity data received from the sensors, various attributes of the detected physical activity. Attributes of the detected physical activity may include, but are not limited to, physical, biological, physiological, and/or environmental characteristics associated with the detected physical activity. Examples of attributes determinable by device 100 upon detecting a physical activity can include, but are not limited to: duration of the detected physical activity; time(s) of a day when the user performs the detected physical activity; amount of Calories burned by a user of the device while performing the detected physical activity; distance traveled by a user of the device while performing the detected physical activity; steps taken by a user of the device while performing the detected physical activity; elevation climbed by a user of the device while performing the detected physical activity; highest/lowest/average velocity of a user of the device while performing the detected physical activity; highest/lowest/average heart rate of a user of the device while performing the detected physical activity; highest/lowest/average body temperature of a user of the device while performing the detected physical activity; or the like. For example, when device 100 may be operative to categorize a detected physical activity as walking, device 100 can further determine one or more attributes of the detected walking, such as a length of time for which the walking continues, highest/lowest/average speed of the user while walking, amount of Calories burned from the detected walking, or the like. In some examples, device 100 can further determine time dimensions associated with one or more attributes using a clock/timer sensor, such as time(s) of a day when physical activity is detected, time(s) of a day when the most/least intensive physical activity is detected, time(s) of a day when a certain amount of Calories are burned, or the like.

Processor 102 may be operative, such as in combination with any sensors of sensor circuitry 112, to detect when device 100 may be placed into a viewing position for a user. For instance, an accelerometer, motion sensor, and/or gyroscope can detect when device 100 is raised, lowered, and shaken. These sensors can also detect wrist rotation forward and backward. In some examples, the raising of device 100 can be interpreted as a placement of the device into viewing position. In other examples, the raising and rotation of device 100 can be interpreted as a placement of the device into viewing position. In yet other examples, the raising and rotation of device 100 within a threshold duration can be interpreted as a placement of the device into viewing position. When put into a viewing position, device 100 can adjust the display image according to the viewing positions and angles, and/or update the display image to reflect the most current data related to the user's physical activity. In some examples, device 100 can determine that when it is moving at a velocity that exceeds a threshold (e.g., 10 miles per hour ("mph"), 20 mph, 25 mph, 30 mph, 40 mph, 50 mph, 55 mph, 60 mph, 65 mph, etc.), the user of the device is commuting, and the movement associated with the user is not a result of the user's bodily movement or exercising. In other examples, device 100 can receive an input from a user indicating that he/she is engaging in a particular type of activity that causes them to move at a velocity exceeding the above-mentioned threshold (e.g., cycling), and that the associated movement should be interpreted as being a result of exercise.

Device 100 may be operative to track a user's physical activity over different lengths of time. For example, if device 100 monitors a user's daily activity, it can track one or more attributes of the user's physical activities performed on the same day and can store and reset the values of those attributes the next day. For instance, in some cases, device 100 can monitor a total amount of daily physical activity performed by the user, and this total amount can be updated in real time throughout the day for 24 hours as more activities are detected. After the 24 hours have passed, the total amount can be stored and reset. Device 100 can be configured to reset the attribute value at a specified time that is adjustable by a user. In other examples, device 100 can operate over different lengths of time, such as a half day, two days, a week, two weeks, a month, or the like, that can be adjustable by a user of device 100. Further, in some examples where device 100 may monitor a user's physical activity over a relatively extended length of time, device 100 may not have enough memory capacity to track and store all of the attributes of the user's physical activities over such an extended length of time and can instead be configured to offload some or all of the data collected from the sensors on an external device (e.g., a remote server) that is remote from device 100. The external device can be configured to communicate with a plurality of devices 100, and store data collected from these devices. The external device can be further configured to execute computer instructions on the data and communicate the result with one or more of these devices 100.

Electronic device 100 may also be provided with a housing 101 that may at least partially enclose one or more of the components of device 100 for protection from debris and other degrading forces external to device 100. In some embodiments, one or more of the components may be provided within its own housing (e.g., input component 108 may be an independent keyboard or mouse within its own housing that may wirelessly or through a wire communicate with processor 102, which may be provided within its own housing).

Figure 2:
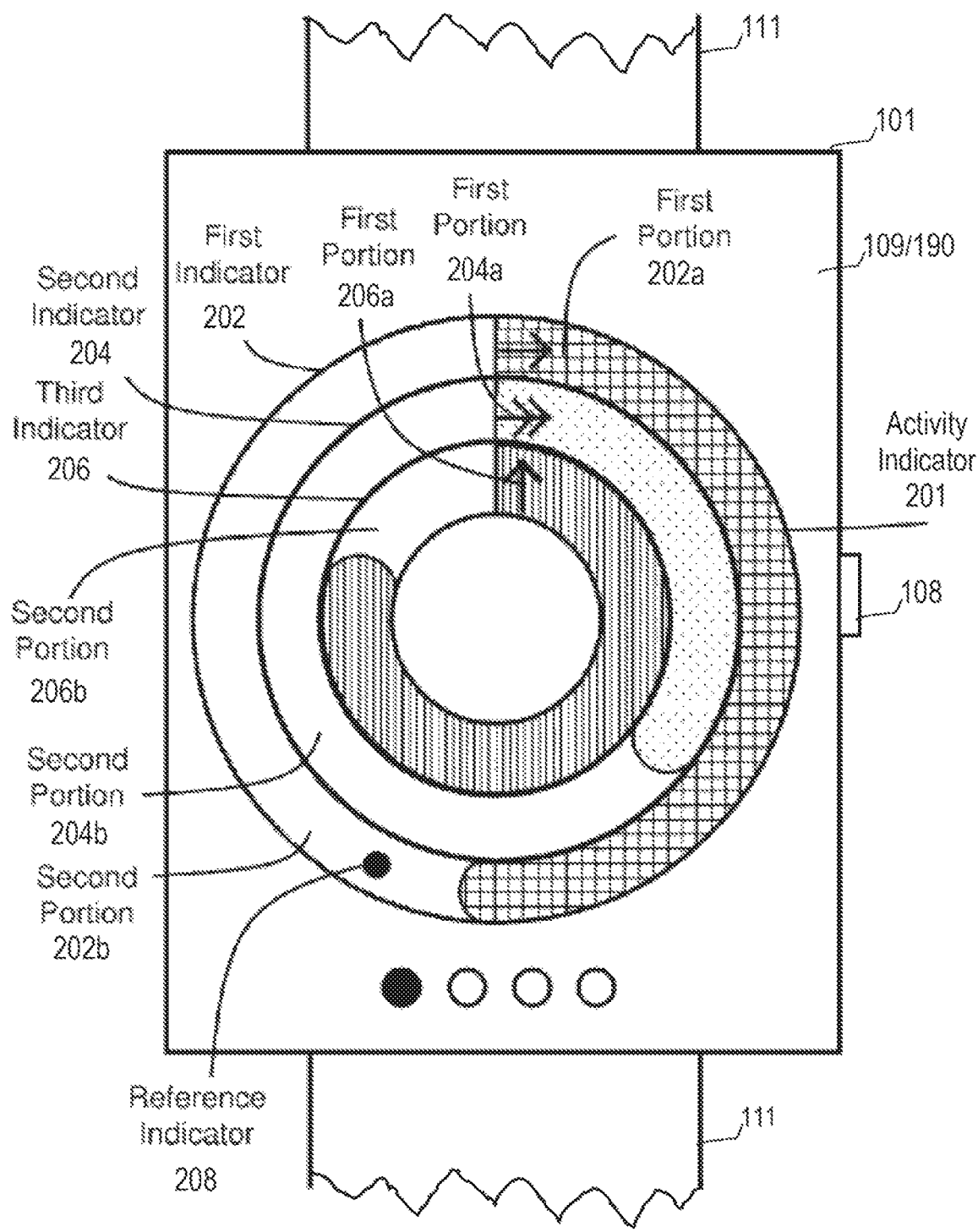
FIG. 2 is a front view of an illustrative example of the electronic device of FIG. 1 presenting an exemplary physical activity monitoring interface.
Figure 2A:
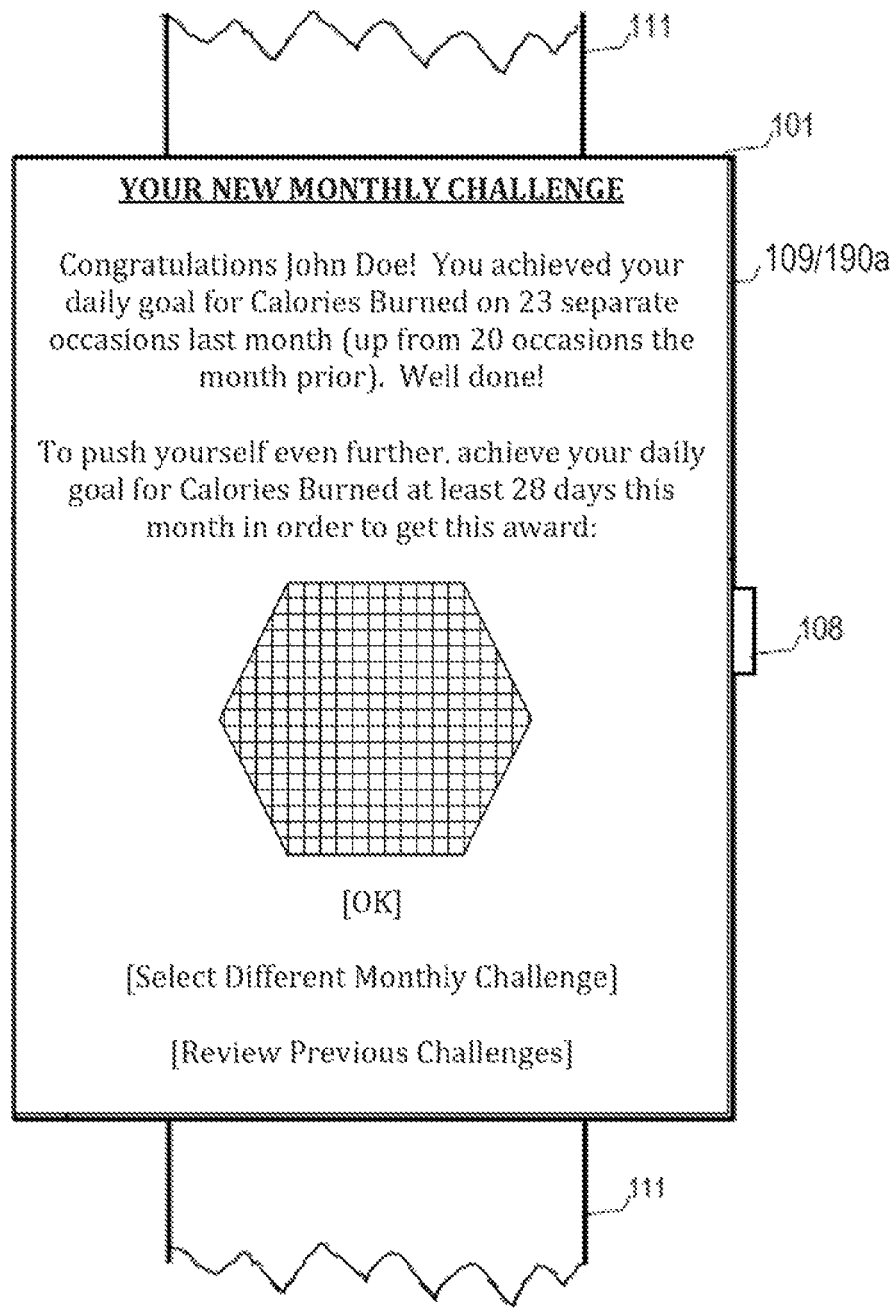
FIGS. 2A-2C are additional exemplary physical activity monitoring and/or motivating interfaces of the electronic device of FIGS. 1 and 2.
Figure 2B:
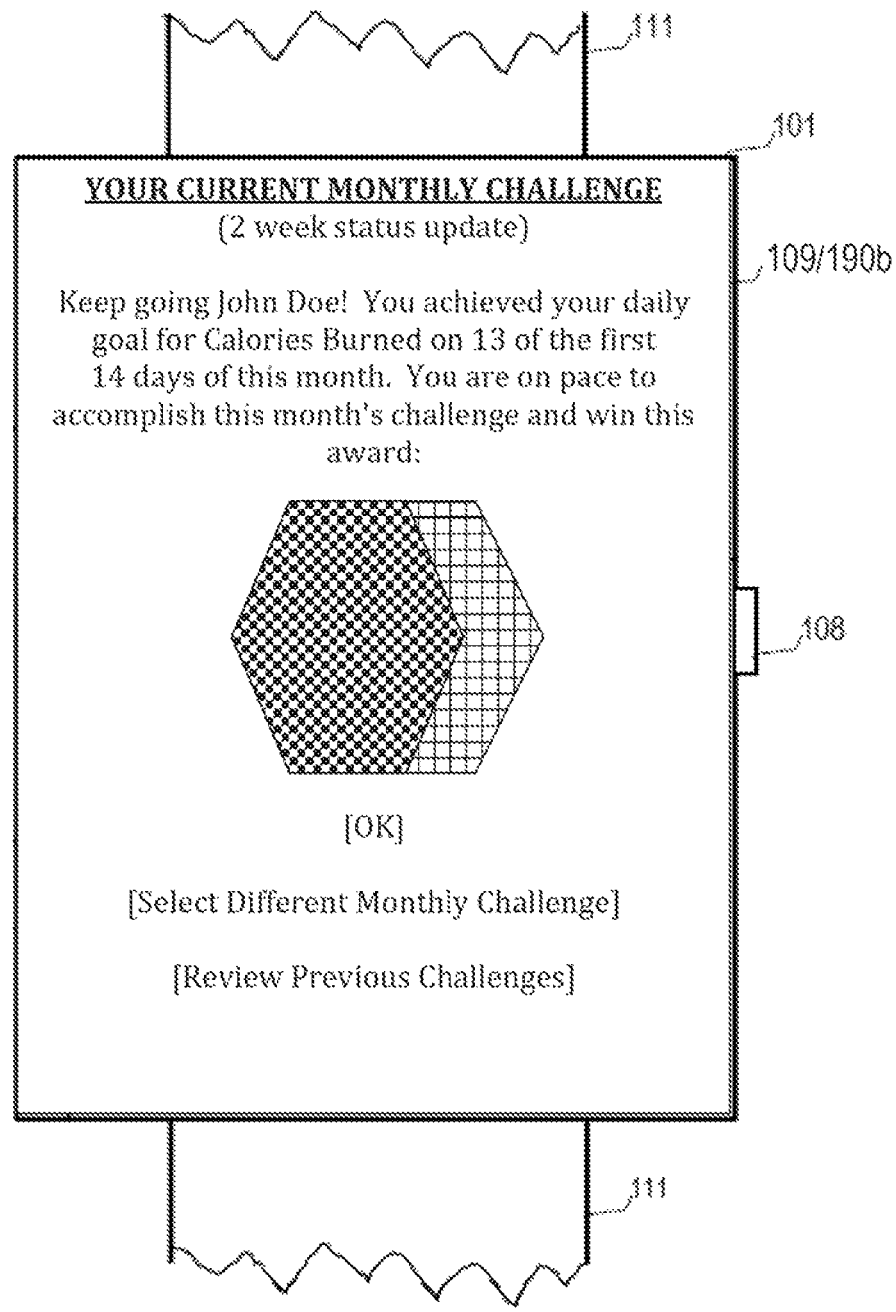
Figure 2C:
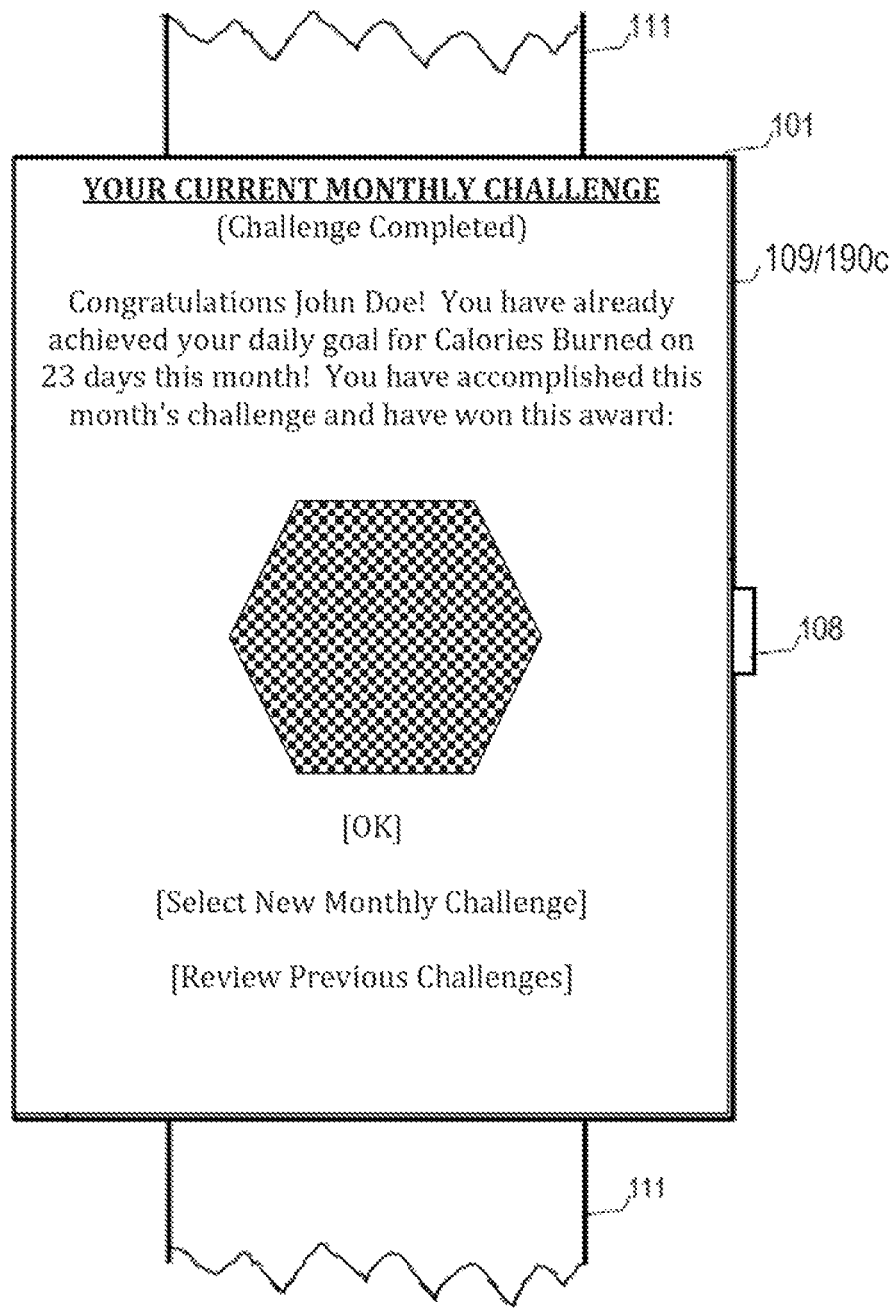

As shown in FIGS. 2-2C, one specific example of electronic device 100 may be a wearable electronic device, such as an Apple Watch™, where housing 101 may allow access to a touch screen I/O component 109, an additional input component 108 (e.g., a push button and/or a rotatable mechanism), an additional output component (e.g., an audio output component and/or haptic component (not shown)), and/or various sensors (not shown), through which device 100 and a user and/or an ambient environment may interface with each other. As shown in FIG. 2, for example, device 100 may include one or more attachment mechanisms 111, which may permit attachment of device 100 with, for example, hats, eyewear, earrings, necklaces, shirts, jackets, bracelets, watch straps, chains, trousers, belts, shoes, purses, backpacks, and so forth such that device 100 may be worn by a user (e.g., around a user's wrist). Attachment mechanism 111 may include any suitable attachment mechanisms, including, but not limited to, a string, a clip, a clasp, a metal loop, a toggle, a button, a snap, a hook, an interlocking part, a soldered part, or the like, that can be attached to or integrated with hats, eyewear, earrings, necklaces, shirts, jackets, bracelets, watch straps, chains, trousers, belts, shoes, purses, backpacks, hairbands, armbands, any other clothing, jewelry, or wearable accessories. In yet other examples, attachment mechanism 111 can include an adhesive, a weld metal, a polymer, a glue, or the like, that permits device 100 to be directly affixed to a user's body part, such as wrist, finger, toe, neck, head, arm, leg, ankle, waist, or the like.

As mentioned, device 100 can be used for detecting and monitoring various attributes of a user's physical activity, such as an amount, an intensity level, a duration, a progress relative to a set value, a trend over a time period, or the like, of the activity, and can generate user interfaces for displaying the same. Device 100 can further be used to monitor a user's inactivity, where the user can be categorized as being inactive when device 100 detects that the user is not engaged in a physical activity that meets a predetermined criteria. For example, inactivity can be characterized by the absence of the user engaging in a physical activity that meets a threshold intensity (e.g., movement that expends a threshold number of Calories per unit time, movement that exceeds a threshold distance per unit time, or the like), the absence of the user engaging in a specified type of activity (e.g., standing, walking, running, swimming, climbing stairs, or the like), or a combination thereof. Such sensors (e.g., in combination with a processor and an output component (e.g., I/O component 109) may be operable to output activity data that represents various attributes of a detected activity of the user (e.g., in a graphic user interface ("GUI") screen 190 of FIG. 2 (e.g., as described in more detail with respect to process 300 of FIG. 3)), which may allow a user to discover attributes about its monitored physical activity and/or information about motivation to be physically active in the future. GUI 180 may include various layers, windows, screens, templates, elements, menus, and/or other components of a currently running application (e.g., application 103) that may be displayed in all or some of the areas of a display output component of I/O component 109. One or more of user input component 108 or of a user input component of I/O component 109 may be used to navigate through any GUI (e.g., to scroll through or select one or more graphical elements or icons of a GUI). Such a touch screen I/O component 109 may employ any suitable type of touch screen input technology, such as, but not limited to, resistive, capacitive, infrared, surface acoustic wave, electromagnetic, or near field imaging. Furthermore, touch screen I/O component 109 may employ single point or multi-point (e.g., multi-touch) input sensing.

Figure 3:
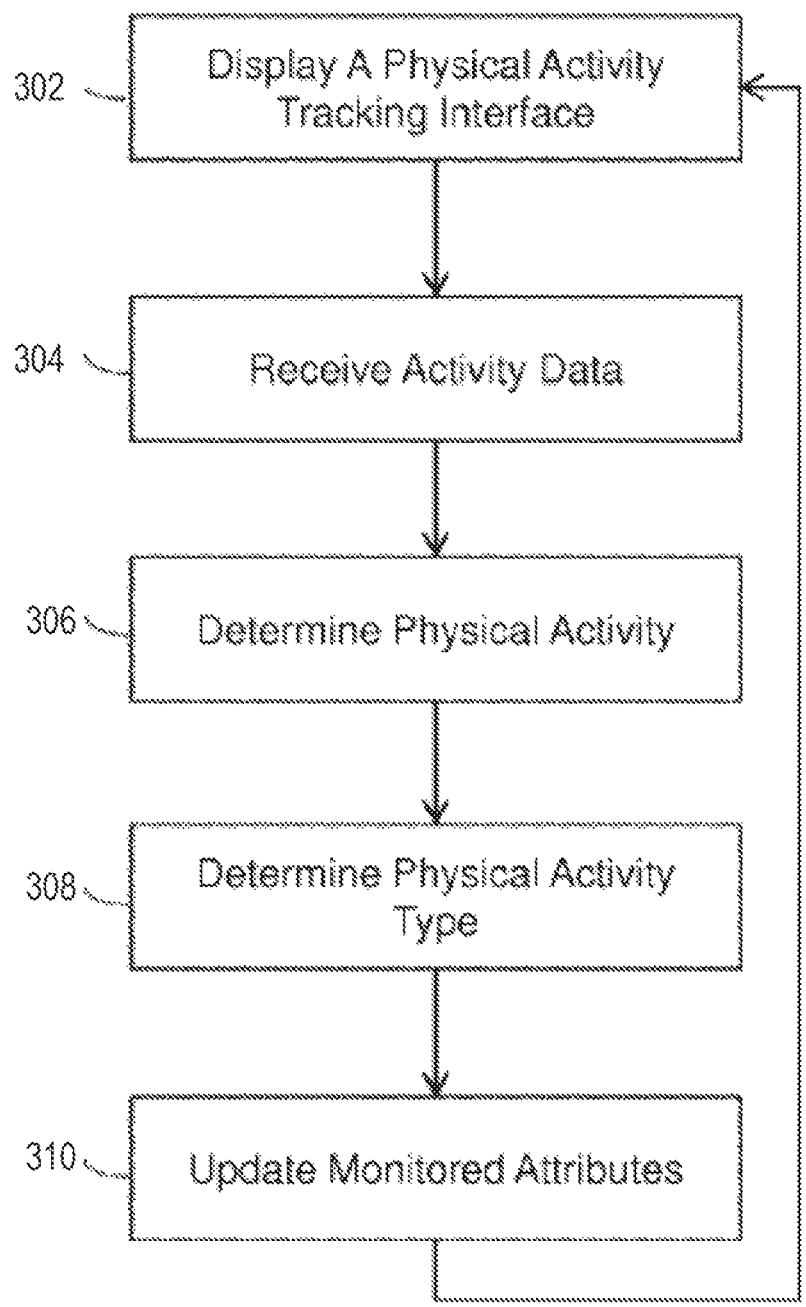
FIGS. 3 and 4 are flowcharts of illustrative processes for generating a physical activity monitoring interface for monitoring a user's physical activity.

FIG. 3 is a flowchart of an illustrative process 300 for operating an electronic device (e.g., a process that may be performed by device 100) for monitoring a user's physical activity and updating a physical activity tracking interface of the device (e.g., an interface of GUI screen 190 of FIG. 2). Process 300 may include detecting movement associated with the device, recognizing the detected movement as being associated with a physical activity performed by a user using the device, monitoring various attributes of the detected physical activity, and presenting one or more attributes of the physical activity on an output component (e.g., a display) of the device. Process 300 may provide an intuitive way to monitor attributes of a user's physical activity or inactivity and generate user interfaces for presenting the same. Process 300 may reduce the cognitive burden on a user when monitoring attributes of the user's physical activity or inactivity, thereby creating a more efficient human-machine interface. For battery-operated computing devices, enabling a user to monitor attributes of the user's physical activity or inactivity and experience user interfaces for presenting the same more quickly and more efficiently may conserve power and increase the time between battery charges.

At operation 302 of process 300, one or more processors of the device can present (e.g., on a display of the device) a physical activity tracking interface. The physical activity tracking interface can include any number of indicators representing any number of monitored attributes of a user's physical activity. The indicators of the physical activity tracking interface can be updated in real-time in response to updates to the values of the monitored attributes of physical activity. In this way, a display of the device can provide real-time information about the user's monitored physical activity. An indicator can include a text, an image, or combination thereof. For example, an animated image can be used to show a progression or otherwise changing status of a monitored attribute. In some examples, operation 302 can further include the presenting additional indicators to provide more information about the monitored attributes, such as a goal value for each of the monitored values, a progressive measure of the monitored values compared to respective goal values, an automatically adjusting goal value based on a passage of time (e.g., 10% of a whole goal value in the morning gradually being adjusted to increase the percentage as the time passes, etc.), a history of past physical activity (e.g., the highest/lowest, or daily average over a month, a week, two days, last day, etc.), any of the above information associated with other users (e.g., the highest/lowest, or daily average amount of physical activity performed by other users different from the user of the device), or the like. Information associated with other users wearing devices other than the device performing process 300 can be collected through an external server that may be configured to communicate with such devices. GUI screen 190 of FIG. 2 may illustrate an exemplary physical activity tracking interface that can be displayed at operation 302 of process 300.

At operation 304 of process 300, one or more processors of the device can receive activity data that is representative of any sensed physical activity of a user from one or more sensors (e.g., any sensor(s) of sensor circuitry 112 of device 100). At operation 306 of process 300, one or more processors of the device can process the received activity data to determine whether the activity data indicates that a physical activity, as opposed to a gesture, has been performed by the user of the device. In some examples, the occurrence of a physical activity by the user can be determined by analyzing the activity data and determining whether it reflects one or more characteristics that are associated with a user performing a physical activity while wearing or otherwise carrying or otherwise interacting with the device. Such characteristics can include, but are not limited to, a minimum displacement per unit time, a speed, a rate of change of body temperature, or the like.

After determining at operation 306 that a physical activity has been performed by the user, one or more processors of the device may determine a type of the detected physical activity at operation 308 of process 300. This determination of operation 308 can be based on at least the activity data and a predetermined set of criteria for a certain type of activity. The device can categorize detected physical activities into any number of categories (e.g., 1 or more) and monitor different attributes for each category. For example, the device can categorize detected physical activities of a user of the device into two or more categories, such as a first type and a second type. In some examples, a first type of physical activity can refer to all detected physical activities of a user of the device, while a second type of physical activity can refer to physical activities that satisfy certain required conditions that, for example, can include having activity intensities equal to or greater than a threshold intensity. Alternatively, a second type of physical activity can refer to physical activities that have intensities less than a threshold intensity. A threshold intensity can be represented as a distance traveled, a number of Calories burned, a number of steps taken, any one or more of these attributes calculated per unit time, or the like. In some examples, the device can adjust a threshold for one or more categories of activities depending on the identified type of the detected physical activity. For instance, the device can categorize activities as being of a second type if they have an activity intensity equal to or greater than a threshold intensity (e.g., a high intensity, an intensity corresponding to a brisk walk, etc.). This threshold intensity can vary depending on whether the detected activity is a walking activity (in which case the threshold can be represented as a minimum number of steps taken per unit time), a running activity (in which case the threshold can be represented as a minimum distance traveled per unit time), or all other types of activity (in which case the threshold can be represented as a minimum number of Calories burned per unit time). It should be appreciated that conditions other than an intensity level can be used to categorize physical activities, for example, such as time(s) of a day when physical activity is detected (e.g., a category for morning activities, another category for day activities, or another category for evening activities, etc.), predetermined type(s) of physical activity (e.g., a category for standing activities, walking activities, running activities, etc.), or the like. One or more conditions can be used alone or in combination to define a category or a type of physical activity.

In some examples, a first type of activity can refer to activity that meets a first set of criteria, a second type of activity can refer to activity that meets a second set of criteria, a third type of activity can refer to activity that meets a third set of criteria, and so on. In the determination process, one or more processor of the device can determine whether the activity data indicates that the associated physical activity meets the first set of criteria, the second set of criteria, and/or the third set of criteria (or other sets of criteria). The criteria can include any information detectable by one or more sensors, such as a speed greater than or equal to a threshold, a minimum number of steps taken per unit time, a minimum amount of Calories burned per unit time, and/or the like. In some examples, the different sets of criteria can be nested such that the third type of activity is a subset of the second type, which can be a subset of the first type. In other examples, the different sets of criteria can cause the types of activity to be mutually exclusive. In yet other examples, the different sets of criteria can cause the types of activity to be partially overlapping.

In some examples, one or more processors of the device can be configured to categorize a user's activity as being a first type of activity representing all forms of physical activity or a second type of activity representing physical activity equal to or greater than a threshold intensity (or, alternatively, less than the threshold intensity). In such cases, a first set of criteria for the first type can simply require that the activity be a physical activity (rather than a gesture) and a second set of criteria for the second type can require that the activity have an intensity greater than or equal to (or, alternatively, less than) a threshold intensity. Intensity can be measured using any number of attributes of an activity, including but not limited to, a distance traveled, a speed, a number of Calories burned, a number of steps taken, any one or more of these attributes calculated per unit time, or the like. Intensity can also be associated with a biological condition that may be detectable by biometric sensors, including but not limited to, a heart rate, an amount of heat, or a rate of change in any of the foregoing conditions, and/or the like. In some examples, the threshold intensity of the second set of criteria can correspond to the intensity of a brisk walk or 3 Metabolic Equivalent of Tasks ("METs"). According to the Centers for Disease Control and Prevention ("CDC"), a brisk walk is walking at a pace of three to three and a half miles per hour or roughly 20 minutes per mile. While example types of physical activity are provided above, it should be appreciated that various other types of physical activity can be used (e.g., standing, running, climbing, etc.).

In some examples, the criteria used by the device to determine type(s) of activity can be pre-set in the device. In other examples, the criteria can be directly input by a user, such that the user can customize which activities are going to be monitored separately from others. In yet other examples, the criteria can be automatically calculated by the device based on the user's health information. The user's health information can be input by a user (e.g., responsive to a user health survey presented by the device) and/or received from an authorized health care provider, for example, and can refer to user's age, weight, gender, body mass index ("BMI"), average heart rate, average blood pressure, or the like. Alternatively, the user's health information can be stored in an external device configured to communicate with the device such that the device can receive the data to generate customized criteria for the user of the device. In other examples, the external device can determine the customized criteria for the user of the device and can transmit the determined criteria to the device.

At operation 310 of process 300, one or more processor(s) of the device can update one, some, or each of the monitored attributes of the detected physical activity. The monitored attributes of the detected activity can be expressed in any standard, arbitrary, or other unit of measurement, such as Calories burned, amount of time spent detecting the activity (e.g., amount of time of exercise), distance traveled, number of steps, and/or the like. The monitored attributes of different types of physical activity can be the same or different. Additionally, the monitored attributes can be stored as values in a memory or storage, and updating the monitored attributes at operation 310 can include updating these stored values. For example, if the detected movement of the device corresponds to a physical activity of a first type and not of any other type, a stored value representing the aggregate amount of the first type of activity can be updated at operation 310, and other stored values representing other types of activity may not be updated. The updating process can be performed in real-time in response to a detection of any new physical activity to the extent that the detected physical activity has attributes that are being monitored by the device.

Operations 302, 304, 306, 308, and 310 can be repeated any number of times and at any desired interval of time to detect a user's physical activity and to update the presentation (e.g., display) of the physical activity tracking interface accordingly. Additionally, it should be appreciated that while operations 302, 304, 306, 308, and 310 are shown in a particular order, operations 302, 304, 306, 308, and 310 can be performed in any order, at the same time, or some of the blocks can be omitted. For example, the physical activity tracking interface can be repeatedly updated at operation 302 while activity data is being received at operation 304 and processed to update the monitored attributes at operations 306, 308, and 310 to provide the user with current or real-time physical activity information. In other examples where the physical activity application is running in the background of the device or while the display of the device is deactivated, operation 302 can be omitted and operations 304, 306, 308, and 310b can repeatedly be performed to monitor the user's physical activity and update the monitored attributes such that an accurate display of the attributes can later be provided to the user when the physical activity application is reopened or the display of the device is activated.

Figure 4:
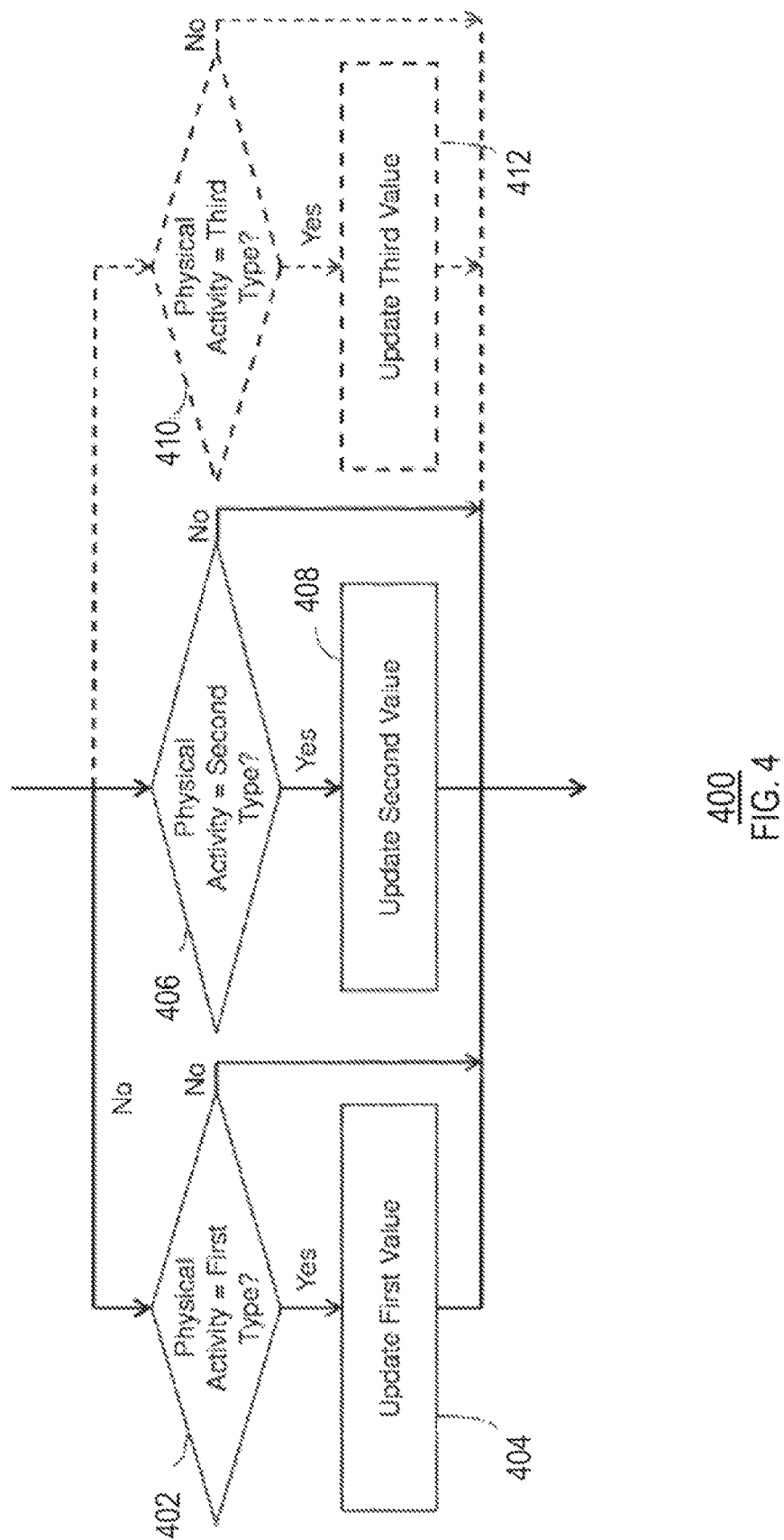

Process 400 of FIG. 4 illustrates an exemplary process for determining a type of physical activity and updating monitored attributes of the type physical activity (e.g., of operations 308 and/or 310 of process 300 of FIG. 3) using device 100 or any other suitable device. For example, process 400 can be used to determine if a physical activity falls within one, some, or each of multiple (e.g., two or more) types of physical activities. In some examples, a first type of physical activity can be a physical activity that meets a first set of criteria, a second type of physical activity can be a physical activity that meets a second set of criteria, and a third type of physical activity can be a physical activity that meets a third set of criteria. In some examples, the first type of activity can be a physical activity detectable by the device, and the second type of activity can be a physical activity that has an intensity greater than or equal to a threshold intensity.

At operation 402 of process 400, activity data, as may be received at operation 304 of process 300, can be used to determine whether the physical activity represented by the activity data corresponds to a first type based on a predetermined first set of criteria. This can include determining whether the physical activity meets each criterion of the first set of criteria. For example, the first set of criteria can simply require that the physical activity be a physical activity (as opposed to a gesture). In this example, operation 402 can include one or more processors of the device determining whether the activity data represents a physical activity rather than a gesture. If it is determined at operation 402 that the physical activity represented by the activity data meets the first set of criteria, process 400 may process to operation 404, during which a first value representing an attribute of the first type of activity can be updated. The attribute can include any desired attribute, such as an amount, an intensity level, a duration, a progress relative to a set value, a trend over a time period, or the like, of the activity. For example, the first value can represent an aggregate amount of active and/or resting Calories expended by the user in performing the first type of activity over a predetermined period of time (e.g., a day). In this example, the updating process performed at operation 404 can include adding, to a previously stored first value (e.g., representing previously measured Calories expended by the user), a value calculated from the activity data that represents an amount of Calories expended by the user in performing the recently detected physical activity. Alternatively, if it is determined at operation 402 that the physical activity represented by the activity data does not meet the first set of criteria, operation 400 can bypass the updating of the first value of operation 404.

Before, during, or after operations 402 and 404, operation 406 of process 400 can be performed to determine whether the physical activity represented by the activity data, as may be received at operation 304 of process 300, corresponds to a second type based on a predetermined second set of criteria. Operation 406 can be similar to operation 402, except that operation 406 can include one or more processors of the device determining whether the physical activity meets each criterion of the second set of criteria. In some examples, the second set of criteria can cause the second type of physical activity to be mutually exclusive from the first type of physical activity. In other examples, the second set of criteria can cause the second type of physical activity to be partially overlapping with the first type of physical activity. In yet other examples, the second set of criteria can encompass the first set of criteria, such that the second type of physical activity can be a subset of the first type of physical activity. For example, the second set of criteria can require that the physical activity have an intensity that is equal to or greater than a threshold intensity (e.g., 3 METS, a threshold movement speed of 3.5 miles per hour or a brisk walk, etc.). In this example, operation 406 can include determining whether the activity data represents the user moving at a speed that is greater than or equal to 3.5 miles per hour (e.g., represents the user exercising). If it is determined that the physical activity represented by the activity data meets the second set of criteria, operation 400 can proceed to operation 408, during which a second value representing an attribute of the second type of activity can be updated. The attribute can include any desired attribute, such as an amount, an intensity level, a duration, a progress relative to a set value, a trend over a time period, or the like, of the activity. For example, the second value can represent a duration of time that the user performs the second type of activity over a predetermined period of time (e.g., a day). In this example, the updating process performed at operation 408 can include adding, to a previously stored second value (e.g., representing a previously measured duration of time that the user was performing the second type of activity), a value calculated from the activity data that represents a duration of time that the user was engaged in the second type of activity in performing the recently detected physical activity. Alternatively, if it is determined at operation 406 that the physical activity represented by the activity data does not meet the second set of criteria, process 400 can bypass the updating of the second value of operation 408.

In some examples, process 400 can include additional determination paths (e.g., a third determination path represented by the dotted path attached to operations 410 and 412) to determine whether the physical activity corresponds to other types of activity. For example, before, during, or after operations 402 and 404 and/or operations 406 and 408, operation 410 of process 400 can be performed to determine whether the physical activity represented by the activity data, as may be received at operation 304 of process 300, corresponds to a third type based on a predetermined third set of criteria. Operation 410 can be similar to operation 402 and/or operation 406, except that operation 410 can include one or more processors of the device determining whether the physical activity meets each criterion of a third set of criteria. In some examples, the third set of criteria can cause the third type of physical activity to be mutually exclusive from the first type of physical activity and/or the second type of physical activity. In other examples, the third set of criteria can cause the second type of physical activity to be partially overlapping. In some examples, the third set of criteria can include both the first set of criteria and the second set of criteria, causing the third type of physical activity to be a subset of the second type and a subset of the first type of physical activities. In other examples, the third set of criteria can be only partially overlapping with the second set of criteria and/or the first set of criteria, or entirely mutually exclusive with respect to both or either set. For example, the first, second, and third sets of criteria can be configured such that the first type includes a physical activity detectable (and recognizable as a physical activity rather than a gesture) by the device, the second type includes only a physical activity that has an intensity equal to or greater than a first threshold intensity (or an activity in which the user is standing), and the third type includes only physical activities that have an intensity lower than a second threshold intensity. It should be appreciated that there can be numerous other ways to configure the criteria. The attributes being monitored and updated for each of the types of activities can be the same or different. For example, the monitored attribute of both the first and second types of activities can be Calories expended. Alternatively, the monitored attribute of the first type of activity can be Calories expended, while the monitored attribute of the second type of activity can be a duration of time performing the second type of activity. Additionally, the period of time over which the various types of activities are monitored can be the same (e.g., hourly, daily, weekly, monthly, seasonally) or different. For example, if different periods are used, the amount of the first type of physical activity can be aggregated over a day, while the amount of the second type of physical activity can be aggregated over two days. It should be appreciated that many other different periods of time can be used to monitor each of the attributes.

While process 400 shows the detection of only three types of activities, it should be appreciated that process 400 can be used to determine any number of physical activity types and to update monitored attributes for those physical activity types. For example, process 400 can continue to determine whether a physical activity corresponds to a fourth type, a fifth type, a sixth type, and so one, each followed by their respective updating process, similar to the process shown in the illustrated example. Additionally, while the operations of process 400 are shown and described in a particular order, it should be appreciated that the operations can be performed in other orders or at the same time. For example, the activity data can be used to determine whether the physical activity corresponds to the first, second, and third types at operations 402, 406, and 410, respectively, at the same time or in any sequential order.

Referring back to process 300 of FIG. 3, after performing process 400 of FIG. 4 at operations 308 and 310, process 300 can return to operation 302. At operation 302, the processor(s) may present, such as on the display of the device, an updated display of the indicators representative of one, some, or each of the monitored values (e.g., the first value, the second value, and the third value). In some examples, the indicators may include a first indicator representing attributes of only the first value, a second indicator representing attributes of only the second value, and a third indicator representing attributes of only the third value. The first, second, and third indicators can be simultaneously displayed on the display or alternatingly displayed. Each of the indicators can include one or more of graphic images, animations, texts or other visual representations. In some other examples, the indicators can include sound effects, haptic effects, and/or any other non-visual effects. Further, one or more indicators can be used to alert the user to the occurrence of certain conditions, such as a continued inactivity of the user for a certain length of time, a detection of a new physical activity, or an achievement of any goal or challenge, or the like. These indicators may advantageously provide a user glancing at the indicators with an overview of their physical activity.

FIGS. 2-2C illustrate different example interfaces that can be displayed on the device during any suitable monitoring and/or motivating processes, such as at operation 302 of process 300. In these examples, the device may be assumed to be a daily activity monitor that categorizes a user's physical activity into a first type (e.g., based on a first set of criteria), a second type (e.g., based on a second set of criteria), a third type (e.g., based on a third set of criteria), and monitors a daily aggregate amount of each type of the user's activity. While specific example parameters are described below, it should be appreciated that different parameters can be used to configure the device. For example, the device can monitor a user's activity over different periods of time (e.g., 5 hours, 6 hours, 12 hours, 24 hours, 48 hours, a week, 2 weeks, 4 weeks, a month, 2 months, 3 months, a season, a year, etc.), can monitor a different number of types of activities (e.g., one, two, three, four, etc.), and/or can monitor different types of activities. Further, the device can monitor attributes other than an aggregate amount for each of the monitored types, such as an average amount over a period of time, a frequency of activity, a maximum or a minimum amount, and/or the like.

FIG. 2 illustrates an example physical activity tracking GUI screen 190 that, for example, can be displayed at operation 302 of process 300. Interface 190 can be updated in real time or any other desired interval of time to reflect current values of the monitored attributes of the user's physical activity, for example, that may be updated at operation 310 of process 300. In some examples, interface 190 can reflect the values representative of the daily total amount of the first type and the second type and the third type of physical activities that are stored in the memory and updated in response to detection of any new physical activity, as explained above in reference to operations 308 and 310 of process 300.

In some examples, the memory of the device can store a first goal value representative of a daily (or any other suitable interval) goal amount for the first type of physical activity, a second goal value representative of a daily goal amount for the second type of physical activity, and a third goal value representative of a daily goal amount for the third type of physical activity. In some examples, the first goal value can be represented in the same measurement metric used to quantify the first type of physical activity, the second goal value can be represented in the same measurement metric used to quantify the second type of physical activity, and the third goal value can be represented in the same measurement metric used to quantify the third type of physical activity. For example, the amount of the first type of activity may be represented using the amount of Calories burned, and thus, the numeric value of the first goal value stored in the memory may represent the goal amount of Calories to be burned by the user (e.g., 300 Calories, 500 Calories, 1000 Calories, 2000 Calories, etc.) in a particular interval of time associated with the goal (e.g., per day). On the other hand, the amount of the second type of activity can be represented using the amount of time spent performing the second type of physical activity, and thus, the numeric value of the second goal value stored in the memory may represent the goal amount of time to be spent by the user for performing high intensity activities (e.g., 30 minutes, 40 minutes, 60 minutes, etc.) in a particular interval of time associated with the goal (e.g., per day). On the other hand, the amount of the third type of activity can be represented using the amount of distance traveled performing the third type of physical activity (e.g., walking, running, swimming, cycling, and/or the like), and thus, the numeric value of the third goal value stored in the memory may represent the goal amount of distance to be traveled by the user (e.g., 3 miles, 4 miles, 5 miles, etc.) in a particular interval of time associated with the goal (e.g., per day).

One, some, or each of the goal values (e.g., the first goal value, the second goal value, and the third goal value) can be directly inputted by a user of the device before the monitoring starts. In other examples, one, some, or each of the goal values can be automatically set by the device based at least on any suitable collected user's health data, which may be stored in the device or in an external device configured to communicate with the device. Health data can include information relating to the user's age, weight, gender, BMI, blood pressure, heart rate, or any other physical conditions. The device and/or the external device can perform predetermined computing instructions (e.g., algorithms) on any portion of the user's health data to automatically determine the goal values. In some examples, one, some, or each of the goal values can be determined based on the user's progress over a certain period of time and/or the training level selected by the user. Moreover, one, some, or each of the goal values can be recalculated periodically based on the user's performance over each previous period of time (e.g., a daily goal for a type of activity may be automatically updated or calculated and presented as an option to be accepted by the user (e.g., at the start of a new week) based on the user's performance relative to the daily goal during the previous week.

As shown, interface 190 can include a combined activity indicator 201 that may have a first visual representation of an attribute of a first type of user activity in the form of first graphic representation or indicator 202 (e.g., an outer ring), a second visual representation of an attribute of a second type of user activity in the form of second graphic representation or indicator 204 (e.g., an intermediate ring), and a third visual representation of an attribute of a third type of user activity in the form of third graphic representation or indicator 206 (e.g., an inner ring). In some examples, first indicator 202 can be controlled and displayed to represent an attribute of the first type of activity. For example, a physical activity can be categorized into any number of types based on a predetermined set of criteria for each type. In some examples, first indicator 202 can further represent a first goal value for the represented attribute of the first type of physical activity. In these examples, the size of first indicator 202 can be scaled such that its size represents the first goal amount, and a portion of first indicator 202 can be marked such that the marked portion represents the actual value of the represented attribute of the first type of activity performed by the user. Alternatively or additionally, first indicator 202 can include a first portion (e.g., portion 202a) that is representative of the value of the represented attribute of the first type of activity performed by the user and a second portion (e.g., portion 202b) that is representative of a difference between the value of the represented attribute of the first type of activity and the first goal value. As shown, the first portion 202a can be given a color or shading that differs from that of the second portion 202b. Further, a ratio between a size of the first portion 202a and a size of the second portion 202b can be equal to a ratio between the total amount of the first type of activity performed by the user and the difference between the total amount of the first type of activity performed by the user and the first goal value. Therefore portion 202a may be operative to show what the user has achieved and portion 202b may be operative to show what the user needs to achieve to complete the goal. A ratio between a size of the first portion and a size of the second portion can be equal to a ratio between the total amount of the first type of activity performed by the user and the difference between the total amount of the first type of activity performed by the user and the first goal value.

In some examples, first indicator 202 can include a visual indicator representative of the type of activity that it represents (e.g., the right-facing arrow at the top of the ring). Additionally, in some examples, the leading edge of the completed portion 202a of the ring can be displayed having a different appearance or texture than the trailing parts of the completed portion 202a of the ring. For example, the leading edge of the completed portion 202a of the ring (e.g., the leading edge as the completed portion traverses the ring in the clockwise direction) can be displayed in a brighter shade of a color, while the trailing parts of the completed portion of the ring can be displayed in a darker shade of the same color. This allows a user to easily view their progress towards the goal. Additionally, in some examples, if the current value of the value represented by first indicator 202 exceeds the goal value, the leading edge of the completed portion 202a of the ring can continue to traverse the ring and overlap a previously completed portion of the ring. By displaying the leading edge using a different shade or texture, the user can distinguish the leading edge from a previously completed portion of the ring.

Activity indicator 201 can further include a second visual representation of an attribute of a second type of user activity in the form of second indicator 204. In some examples, second indicator 204 can be controlled and displayed to represent an attribute of the second type of activity. For example, a physical activity can be categorized into any number of types based on a predetermined set of criteria for each type. The criteria can include any attribute of the physical activity or information detectable by the activity sensors, such as a speed greater than or equal to a threshold, a minimum number of steps taken per unit time, a minimum amount of Calories burned per unit time, and/or the like. For example, the second set of criteria for the second type of physical activity can require that the physical activity have an intensity greater than or equal to (or, alternatively, less than) a threshold intensity, such as an intensity corresponding to a brisk walk or moving at a speed equal to or greater than 3 miles per hour. Alternatively, second indicator 204 can represent a second value of any attribute of the physical activity, such as an amount, an intensity level, a duration, a progress relative to a set value, a trend over a time period, or the like, of the activity. For example, the second value can represent an aggregate duration of time that the user performed the second type of activity over a predetermined period of time (e.g., a day).

In some examples, second indicator 204 can further represent a second goal value for the represented attribute of the second type of physical activity. In these examples, the size of second indicator 204 can be scaled such that its size represents the second goal amount, and a portion of second indicator 204 can be marked such that the marked portion represents the actual value of the represented attribute of the second type of activity performed by the user. Alternatively or additionally, second indicator 204 can include a first portion (e.g., portion 204a) that may be representative of the value of the represented attribute of the second type of activity performed by the user and a second portion (e.g., portion 204b) that may be representative of a difference between the value of the represented attribute of the second type of activity and the second goal value. As shown, first portion 204a can be given a color or shading that differs from that of second portion 204b. Further, a ratio between a size of first portion 204a and a size of second portion 204b can be equal to a ratio between the total amount of the second type of activity performed by the user and the difference between the total amount of the second type of activity performed by the user and the second goal value.

In some examples, second indicator 204 can include a visual indicator representative of the type of activity that it represents (e.g., the double right-facing arrow at the top of the ring). Additionally, in some examples, the leading edge of the completed portion 204a of the ring can be displayed having a different appearance or texture than the trailing parts of the completed portion 204a of the ring. For example, the leading edge of the completed portion 204a of the ring (e.g., the leading edge as the completed portion traverses the ring in the clockwise direction) can be displayed in a brighter shade of a color, while the trailing parts of the completed portion of the ring can be displayed in a darker shade of the same color. This allows a user to easily view their progress towards the goal. Additionally, in some examples, if the current value of the value represented by indicator 204 exceeds the goal value, the leading edge of the completed portion 204a of the ring can continue to traverse the ring and overlap a previously completed portion of the ring. By displaying the leading edge using a different shade or texture, the user can distinguish the leading edge from a previously completed portion of the ring.

Activity indicator 201 can further include a third visual representation of an attribute of a user's inactivity in the form of third indicator 206. In some examples, third indicator 206 can be controlled and displayed to represent an attribute of the third type of activity. For example, third indicator 206 can represent a distance traveled during a predetermined type of activity (e.g., walking, running, swimming, cycling, etc.). In these examples, the size of third indicator 206 can be scaled such that its size represents a predetermined (or goal) number of distance segments that are each equal to a predetermined distance or any other suitable third goal amount. In these examples, a portion of third indicator 206 can be marked such that the marked portion represents the number of segments of distance traveled for the predetermined type of activity. For example, the predetermined number of distance segments can be equal to 5 and the predetermined distance of each of these segments can be 1 mile. In some examples, third indicator 206 can include a visual indicator representative of the type of activity that it represents (e.g., the upward-facing arrow at the top of the ring). In these examples, the size of third indicator 206 can be scaled such that its size represents the third goal amount, and a portion of third indicator 206 can be marked such that the marked portion represents the actual value of the represented attribute of the third type of activity performed by the user. Alternatively or additionally, third indicator 206 can include a first portion (e.g., portion 206a) that may be representative of the value of the represented attribute of the third type of activity performed by the user and a second portion (e.g., portion 206b) that may be representative of a difference between the value of the represented attribute of the third type of activity and the third goal value. As shown, first portion 206a can be given a color or shading that differs from that of second portion 206b. Further, a ratio between a size of first portion 206a and a size of second portion 206b can be equal to a ratio between the total amount of the third type of activity performed by the user and the difference between the total amount of the third type of activity performed by the user and the third goal value. In some examples, the leading edge of the completed portion 206a of the ring can be displayed having a different appearance or texture than the trailing parts of the completed portion 206a of the ring. For example, the leading edge of the completed portion 206a of the ring (e.g., the leading edge as the completed portion traverses the ring in the clockwise direction) can be displayed in a brighter shade of a color, while the trailing parts of the completed portion of the ring can be displayed in a darker shade of the same color. This allows a user to easily view their progress towards the goal. Additionally, in some examples, if the current value of the value represented by indicator 206 exceeds the goal value, the leading edge of the completed portion 206a of the ring can continue to traverse the ring and overlap a previously completed portion of the ring. By displaying the leading edge using a different shade or texture, the user can distinguish the leading edge from a previously completed portion of the ring.

Respective size of the first and second portions of each ring indicator can be updated in real-time to reflect the most current progressive measure of the total amount of the indicator's associated activity, as compared to the goal value of the indicator. For example, as additional activity is detected, portion 202a can be increased in size and portion 202b can be decreased in size to give the appearance that the leading edge of portion 202a is traveling in a clockwise direction along outer ring 202, and ring portions 202a and 202b can be scaled such that a ratio between the entire circumference of ring 202 and ring portion 202a is equal to a ratio between the first goal value and the total amount of activity performed by the user towards that first goal value during the time interval that may be associated with interface 190 (e.g., a current day).

Interface 190 can further include a reference indicator representing supplemental information relevant to the user's activity on any of the first, second, or third indicators 202, 204, or 206. In the illustrated example, the additional reference indicators are shown as reference indicator 208 along the ring of first indicator 202. Examples of supplemental information that can be additionally provided on the display include, non-exclusively, timed-based goals that are adjusted in accordance with a passage of time (e.g., certain percentage(s) of the goal to be completed by certain time(s) of a day, such as 10% to be completed by 10:00 am, 80% to be completed by 9:00 pm, and/or the like. such that the indicator would be moving along the ring throughout the day to indicate the changing percentage of the goal to be completed depending on the time of a day), history of user's past activity (e.g., activity performed by a user of device 100 on a particular day of the week, a highest/lowest or daily average amount of activity of a certain category performed by the user of the device over a month, a week, two days, last day, etc.), activity data of other users different from the user of the device (e.g., a highest/lowest, or daily average amount of activity of certain category performed by other users different from the user of the device), or the like.

The first goal value of outer ring 202 can be 1,000 Calories, the second goal value of intermediate ring 204 can be 60 minutes of exercise, and the third goal value of inner ring 306 can be 5 miles of distance traveled via physical activity. In other words, the user's goal is to burn at least 1,000 Calories a day (or for any other time interval associated with interface 190) regardless of the types of physical activity performed, to perform at least 60 minutes of exercise or activity above a certain threshold intensity per day a day (or for any other time interval associated with interface 190), and to travel at least 5 miles due to exercise or other suitable physical activity per day a day (or for any other time interval associated with interface 190). A text indicator (not shown) may be provided on interface 190 that may indicate information similar to that of one or more of indicators 202, 204, and 206, such as textual information that may indicate that the user has "burned a total of 500 Calories of the 1,000 Calorie goal, exercised for a total of 20 minutes of the 60 minute goal, and traveled a total of 4 miles of the 5 mile goal." While visually distinct parts of each one of rings 202, 204, and 206 may permit a user of the device to readily recognize relative progressive measures of the monitored activity (e.g., filled areas 202a, 204a, and 206a versus empty areas 202b, 204b, and 206b), it is noted that different effects may be used to make the visual distinction, examples of which may include, but are not limited to, applying different colors, hues, shapes, images, animations, intensity, brightness, or other effects of the same sort.

Other interfaces can be displayed to provide additional information associated with the attributes represented by the indicators of interface 190. These other interfaces can be displayed in response to a tap, swipe, or other gesture performed while interface 190 is displayed on the device.

For example, another interface (not shown) can be displayed in response to a swipe gesture performed from right to left of the display while interface 190 is displayed, where such another interface may be representative of first indicator 202 of interface 190 and its portions 202*a* and 202*b* and/or text representation of the current value of the attribute represented portion 202*a* and text representation of the goal value attribute represented by first indicator 202 (e.g., text representation that may indicate that first portion 202*a* represents 300 Calories and text representation that may indicate that the entire first indicator 202 represents a goal value of 600 Calories). Various other interfaces may be similarly accessed for presenting textual or other information for other indicators of interface 190.

Additionally or alternatively, an activity type and associated goal may be any suitable type of workout with an associated goal. Device 100 may be configured to receive a selection of a particular workout to be conducted by the user, detect movement associated with the device during the workout, recognize it as being associated with a physical activity performed by the user using the device, monitor various attributes of the detected physical activity, determine attributes of the workout based on the monitored attributes of the detected physical activity, and present and/or otherwise track one or more of the attributes of the workout. A selected type of workout can include any type of workout, such as running, walking, cycling, swimming, yoga, dancing, climbing, cross-training, rowing, or the like. A goal for a type of workout selected can include an identification of an attribute of the selected workout (e.g., a distance, a duration, a number of Calories burned, a pace, or the like) and a goal value for the attribute. For example, for a running type of workout, the goal can include a distance attribute and a value of 3 miles, while another example goal can include a duration attribute and a value of 45 minutes, or a Calorie attribute and a value of 500 Calories. Therefore, device 100 may be operative to determine a number of workouts completed by a user over any suitable time interval, where a workout may be defined in any suitable manner, such as at least 15 minutes of uninterrupted physical activity of at least a certain threshold intensity.

A summary interface may be presented by device 100 at the end of any suitable time interval (e.g., calendar interval). For example, when daily goals may be associated with the different types of physical activity that may be monitored by device 100, as described with respect to processes 300 and 400 and interface 190 (e.g., daily goals of 1,000 calories burned, 60 minutes of exercise, and 5 miles traveled), device 100 may be operative at the end of each day to provide an interface (not shown) summarizing which goal(s) were completed or not completed and/or how well the user did with respect to each goal. Additionally or alternatively, at the end of a larger time interval that may include multiple ones of a time sub-interval that may be associated with the goals (e.g., a week time interval including 7 day time sub-intervals, etc.), a summary interface (not shown) can be presented (e.g., at the end of a week when the goals of interface 190 may be daily goals). Such a summary interface can include a text description of the user's performance over the week with respect to one or more goals. For example, at the end of such a time interval (e.g., week), such a summary interface can indicate any suitable time interval user activity values for the previous time interval, including, but not limited to, the number of days during the week that the user met or exceeded its daily expended Calorie goal (e.g., the goal represented by outer ring 202 of activity indicator 201), the number of days during the week that the user met or exceeded a magnitude (e.g., 150%, twice, thrice, etc.) its daily expended Calorie goal, the total expended Calories during the week, the daily average expended Calories expended for the days of the week, the number of days during the week that the user met or exceeded its daily time exercised goal (e.g., the goal represented by intermediate ring 204 of activity indicator 201), the number of days during the week that the user met or exceeded a magnitude of its daily expended time exercised goal, the total amount of time exercised during the week, the daily average amount of time exercised for the days of the week, the number of days during the week that the user met or exceeded its daily distance traveled goal (e.g., the goal represented by inner ring 206 of activity indicator 201), the number of days during the week that the user met or exceeded a magnitude of its daily distance traveled goal, the total amount of distance traveled during the week, the daily average amount of distance traveled for the days of the week, and/or the number of workouts that the user completed during the week. In addition, the electronic device may be operative calculate a new time sub-interval (e.g., daily) goal for the user for one or more of the activity types to be used for the next time interval (e.g., next week) based on the user's performance during the previous time interval (e.g., the week that just completed) and can present the new goal suggestion(s) to the user. The user can accept a new goal as the goal to be used for the next week or can modify the goal up or down based on the user's preference.

In addition to or as an alternative to adjusting or recommending the adjustment of one of more time sub-interval goals (e.g., daily goals) of a time sub-interval based on past user performance with respect to such time sub-interval goals over a time interval including two or more of such time sub-intervals (e.g., adjusting a daily goal for an upcoming week based on the user's performance over the previous week), device 100 may be operative to provide a challenge to a user for an upcoming time interval based on the user's performance over at least one previous time interval. Such a challenge for an upcoming time interval may not be an adjustment to any time sub-interval goals for the upcoming time interval, but, instead, such a challenge for an upcoming time interval may be defined so that it may be achieved by a user satisfying one or more time sub-interval goals for the upcoming time interval, whatever those goals may be. A challenge for an upcoming time interval (e.g., a month that is just about to begin) may be based on any suitable user activity data detected during the previous time interval (e.g., the month just ending) and/or two or more previous time intervals (e.g., the month just ending and the month just prior to that). A challenge for an upcoming time interval may be proposed at the end of each time interval. Alternatively, in some embodiments, a challenge for an upcoming time interval may only be proposed at the end of another time interval if a certain usage condition was met during that other time interval, such as a condition that the user actively used the device for at least a threshold portion of that time interval (e.g., activity data must be received by device 100 (e.g., at operation 304) during more than 50% of that time interval (e.g., during at least 16 days of a 30 day month) in order for device 100 to propose a challenge to a user for the next time interval. A challenge may be of any suitable challenge type, based on a particular type of user activity value that may be determined based on the past user activity data used to define the challenge. A particular challenge type may be based on any suitable particular type of time interval user activity value that may be identified from user activity data detected during a time interval, including, but not limited to, any of the following types of user activity values for a time interval that includes two or more time sub-intervals:

(1) the number of time sub-intervals for which a first time sub-interval goal was satisfied during the time interval (e.g., a Calories burned time sub-interval goal (e.g., 1,000 Calories burned per day));

(2) the number of time sub-intervals for which a second time sub-interval goal was satisfied during the time interval (e.g., a time exercised time sub-interval goal (e.g., 60 minutes of exercise per day));

(3) the number of time sub-intervals for which a third time sub-interval goal was satisfied during the time interval (e.g., a distance traveled time sub-interval goal (e.g., 5 miles traveled per day));

(4) the number of time sub-intervals for which each one of the first, second, and third time sub-interval goals (or any other combination of two or more time-sub interval goals) was satisfied during the time interval;

(5) the number of time sub-intervals for which a first time sub-interval goal was doubly (or by any other factor) satisfied during the time interval (e.g., the number of days in the month where at least 2,000 Calories were burned while the first daily goal was 1,000 Calories burned);

(6) the number of time sub-intervals for which a second time sub-interval goal was doubly (or by any other factor) satisfied during the time interval (e.g., the number of days in the month where at least 120 minutes of exercise occurred while the second daily goal was 60 minutes of exercise per day);

(7) the number of time sub-intervals for which a third time sub-interval goal was doubly (or by any other factor) satisfied during the time interval (e.g., the number of days in the month where at least 10 miles were burned while the third daily goal was 5 miles traveled per day);

(8) the number of time sub-intervals for which each one of the first, second, and third time sub-interval goals (or any other combination of two or more time-sub interval goals) was doubly (or by any other factor) satisfied during the time interval;

(9) the total amount of a first type of activity (e.g., Calories burned) monitored during the time interval;

(10) the total amount of a second type of activity (e.g., exercise time) monitored during the time interval;

(11) the total amount of a third type of activity (e.g., distance traveled) monitored during the time interval;

(12) the total number of workouts completed during the time interval;

(13) the average amount of a first type of activity (e.g., Calories burned) monitored per time sub-interval during the time interval;

(14) the average amount of a second type of activity (e.g., exercise time) monitored per time sub-interval during the time interval; and

(15) the average amount of a third type of activity (e.g., distance traveled) monitored per time sub-interval during the time interval.

These types of user activity values and, thus, types of challenges, are just exemplary and many other user activity value types and challenge types may also be used. For example, while calories burned, time exercised, and distance traveled may be three time sub-interval goal types and/or three activity types that may be used to define particular user activity value types, various other activity types and sub-interval goal types may additionally or alternatively be handled and used to define a particular a user activity value type, including, but not limited to, altitude climbed, detected heart beats, weight lifted, and/or the like.

Each challenge type may be operative to identify a particular current state of two or more possible states of the challenge type based on the user activity value for the challenge type's user activity value type as may be determined from user activity data detected during a previous time interval if not also based on the user activity value for the challenge type's user activity value type as may be determined from user activity data detected during at least one other previous time interval, and the identified particular current state may be associated with a particular type of challenge to be issued by that challenge type for an upcoming time interval. As shown in table 900 of FIG. 9, a challenge type for a user activity value type may define two or more states (e.g., two or more of states 1-10 of table 900), each of which may be dependent on a user activity value B that may be indicative of the user activity value of the user activity value type of the challenge type as may be determined based on analysis of user activity data detected during a past time interval TIB (e.g., a most recently completed time interval), and at least some of which may also be dependent on a user activity value A that may be indicative of the user activity value of the user activity value type of the challenge type as may be determined based on analysis of user activity data detected during another past time interval TIA (e.g., a time interval that occurred before (e.g., just before) time interval TIB). As just one example, for a first challenge type for a first user activity value type (e.g., activity value type (1) of the above-list), user activity value B for that first challenge type may be the number of time sub-intervals of time interval TIB for which a Calories burned time sub-interval goal was satisfied, while user activity value A for that first challenge type may be the number of time sub-intervals of time interval TIA for which a Calories burned time sub-interval goal was satisfied. As another example, for a second challenge type for a second user activity value type (e.g., activity value type (2) of the above-list), user activity value B for that second challenge type may be the number of time sub-intervals of time interval TIB for which a time exercised time sub-interval goal was satisfied, while user activity value A for that second challenge type may be the number of time sub-intervals of time interval TIA for which a time exercised time sub-interval goal was satisfied.

Each challenge type may be operative to identify a particular current state from two or more possible states of the challenge type based on at least user activity value B for that challenge type, if not also based on user activity value A for that challenge type. As shown in table 900 of FIG. 9, a challenge type for a user activity value type may define two or more possible states associated with that challenge type (e.g., two or more of states 1-10), where each state may be dependent upon at least one of user activity value B and user activity value A. Each state may include at least one condition based on at least one of user activity values A and B. Each state may also include a challenge for an upcoming time interval TIC (e.g., a time interval following (e.g., directly following) time interval TIB) that may be proposed by the challenge type when each condition of the state of the challenge type is determined to be satisfied, where the challenge may define a user activity value C indicative of a value for the user activity value type of the challenge's challenge type that may be provided as a challenge to a user, such that in order to achieve the challenge the user would have to be physically active enough during time interval TIC such that the physical activity data detected by device 100 would be indicative of that user activity value C for the user activity value type of the challenge's challenge type. A challenge may be designed to motivate a user to beat or repeat an accomplishment of a previous time interval TIB in an upcoming time interval TIC, dependent upon the magnitude of user activity value B and/or a comparison of the magnitude of user activity value B to the magnitude of user activity value A. Such a beat or repeat (e.g., a peak or progress) paradigm may be operative to encourage a user to lead a more active lifestyle in a manner that may not be too daunting so as to risk turning a user off. Moreover, by defining a proposed challenge using actual previous accomplishments of a user, the challenge may be customized to a specific user based on that user's actual previous physical activity and how that activity has changed from one time interval to the next (e.g., from time interval TIA to time interval TIB for customizing a challenge for time interval TIC). The condition(s) of only one state of a challenge type may be satisfied by a particular value B or by a combination of a particular value B and a particular value A, such that only one challenge for an upcoming time interval TIC may be proposed by the challenge type for particular detected user activity data. A particular challenge type may be configured to define or otherwise utilize any suitable possible states, including, but not limited to, any one or more of states 1-10 of table 900 and/or any other state, each of which may include at least one condition based on at least one of user activity values A and B and an associated challenge defining a particular user activity value C that may be proposed for a user to attempt to achieve during time interval TIC.

State 1 of table 900 may include a first condition that may be satisfied only if user activity value B may be classified as "perfect" for the user activity value type of the state's challenge type, and if that condition is satisfied, then the state may not be used to propose a challenge based on the user activity value type of the state's challenge type. The requirements for such a perfect classification may vary based on the user activity value type of the state's challenge type, but such a classification may be indicative of a user accomplishment during time interval TIB that is too good to warrant challenging a user to beat or repeat that accomplishment again (e.g., in the next time interval following the interval during which that accomplishment was achieved). For example, a perfect classification for a user activity value type indicative of the number of time sub-intervals for which a particular time sub-interval goal was satisfied during the time interval (e.g., a Calories burned time sub-interval goal (e.g., 1,000 Calories burned per day)) may be defined as a user activity value indicative of at least 75% of the maximum total value (e.g., at least 24 for a 31 day month) or as a user activity value indicative of at least 3 distinct sets of 7 consecutive time sub-intervals with a daily goal achieved (e.g., each one of at least 3 weeks within a month had the daily goal for all 7 of its days satisfied), or the like. As another example, a perfect classification for a user activity value type indicative of the average amount of a particular type of activity (e.g., Calories burned) monitored per time sub-interval during the time interval may be defined as a user activity value achieved during a time interval within which a daily goal of a time sub-interval was increased by a user at least a particular number of times (e.g., if the user (e.g., through active user selection) increased a Calories burned daily goal at least three times within a month), or the like.

State 2 of table 900 may include a first condition that may be satisfied only if user activity value B may not be classified as "perfect" for the user activity value type of the state's challenge type (e.g., as described with respect to state 1) and a second condition that may be satisfied only if user activity value B is less than a threshold value $\varphi$, and if each of those conditions is satisfied, then a challenge may be proposed by the state that challenges a user to generate a user activity value C that is equal to user activity value B plus 1. The value of such a threshold value $\varphi$ may vary based on the user activity value type of the state's challenge type, but failure to meet such a threshold value $\varphi$ may be indicative of a user accomplishment during time interval TIB that is not sufficient enough to warrant challenging a user merely to repeat the accomplishment, but warrants challenging the user to beat the achievement by an incremental amount. For example, for a user activity value type indicative of the number of time sub-intervals for which a particular time sub-interval goal was satisfied during the time interval (e.g., a Calories burned time sub-interval goal (e.g., 1,000 Calories burned per day)), threshold value $\varphi$ may be equal to 11 for a monthly time interval challenge (e.g., just greater than 33% of the total number of time sub-intervals of the time interval). In some embodiments, such a state 2 may only be provided for challenge types associated with user activity value types that may be indicative of a number of time sub-interval goals satisfied.

State 3 of table 900 may include a first condition that may be satisfied only if user activity value B may not be classified as "perfect" for the user activity value type of the state's challenge type (e.g., as described with respect to state 1) and a second condition that may be satisfied only if user activity value B is not less than a threshold value $\varphi$ (e.g., as described with respect to state 2) and a third condition that may be satisfied only if user activity level B is greater than a threshold percentage $\alpha$ of user activity level A, and if each of those conditions is satisfied, then the state may not be used to propose a challenge based on the user activity value type of the state's challenge type. The value of such a threshold percentage $\alpha$ may vary based on the user activity value type of the state's challenge type, but the user accomplishment of achieving user activity value B that is greater than the prior accomplishment of user activity value A by such a percentage may be indicative of a user accomplishment during time interval TIB that beats the user accomplishment during time interval TIA by an amount too great to warrant challenging a user to beat or even repeat that accomplishment again (e.g., in the next time interval following time interval TIB). For example, such a threshold percentage $\alpha$ may be 130% (e.g., such that value B is more than 30% greater than value A) or any other suitable percentage.

State 4 of table 900 may include a first condition that may be satisfied only if user activity value B may not be classified as "perfect" for the user activity value type of the state's challenge type (e.g., as described with respect to state 1) and a second condition that may be satisfied only if user activity value B is not less than a threshold value $\varphi$ (e.g., as described with respect to state 2) and a third condition that may be satisfied only if user activity level B is not greater than a threshold percentage $\alpha$ of user activity level A (e.g., as described with respect to state 3) and a fourth condition that may be satisfied only if user activity level B is greater than a threshold percentage $\beta$ of user activity level A, and if each of those conditions is satisfied, then a challenge may be proposed by the state that challenges a user to generate a user activity value C that is equal to user activity value B. The value of such a threshold percentage $\beta$ and of such a threshold percentage $\alpha$ may vary based on the user activity value type of the state's challenge type, but an achievement of user activity value B being within a percentage range of α and β of user activity value A may be indicative of a user accomplishment during time interval TIB that sufficiently beats the user accomplishment during time interval TIA to warrant challenging a user merely to repeat the accomplishment of time interval TIB rather than to beat that accomplishment. For example, threshold percentage α may be 130% and threshold percentage β may be 120% (e.g., such that value B is no greater than 30% greater than value A and such that value B is greater than 20% greater than value A) or any other suitable percentages.

State 5 of table 900 may include a first condition that may be satisfied only if user activity value B may not be classified as "perfect" for the user activity value type of the state's challenge type (e.g., as described with respect to state 1) and a second condition that may be satisfied only if user activity value B is not less than a threshold value φ (e.g., as described with respect to state 2) and a third condition that may be satisfied only if user activity level B is not greater than a threshold percentage β of user activity level A (e.g., as described with respect to state 4) and a fourth condition that may be satisfied only if user activity level B is greater than a threshold percentage δ of user activity level A, and if each of those conditions is satisfied, then a challenge may be proposed by the state that challenges a user to generate a user activity value C that is equal to a threshold percentage ε of user activity value B. The value of such a threshold percentage δ and of such a threshold percentage β may vary based on the user activity value type of the state's challenge type, but an achievement of user activity value B being within a percentage range of β and δ of user activity value A may be indicative of a user accomplishment during time interval TIB that beats the user accomplishment during time interval TIA by a relative amount to warrant challenging a user beat that accomplishment of time interval TIB by threshold percentage ε rather than merely to repeat that accomplishment. For example, threshold percentage β may be 120% and threshold percentage δ may be 110% (e.g., such that value B is no greater than 20% greater than value A and such that value B is greater than 10% greater than value A) or any other suitable percentages, while threshold percentage ε may be 120% (e.g., such that value C is 20% greater than value B) or any other suitable percentage.

State 6 of table 900 may include a first condition that may be satisfied only if user activity value B may not be classified as "perfect" for the user activity value type of the state's challenge type (e.g., as described with respect to state 1) and a second condition that may be satisfied only if user activity value B is not less than a threshold value φ (e.g., as described with respect to state 2) and a third condition that may be satisfied only if user activity level B is not greater than a threshold percentage δ of user activity level A (e.g., as described with respect to state 5) and a fourth condition that may be satisfied only if user activity level B is greater than user activity level A, and if each of those conditions is satisfied, then a challenge may be proposed by the state that challenges a user to generate a user activity value C that is equal to a threshold percentage ζ of user activity value B. The value of such a threshold percentage δ may vary based on the user activity value type of the state's challenge type, but an achievement of user activity value B being within a percentage range of δ and 100% of user activity value A may be indicative of a user accomplishment during time interval TIB that beats the user accomplishment during time interval TIA by a relative amount to warrant challenging a user to beat that accomplishment of time interval TIB by threshold percentage ζ rather than merely to repeat that accomplishment. For example, threshold percentage δ may be 110% (e.g., such that value B is no greater than 10% greater than value A and such that value B is greater than 100% of value A) or any other suitable percentages, while threshold percentage ζ may be 110% (e.g., such that value C is 10% greater than value B) or any other suitable percentage.

State 7 of table 900 may include a first condition that may be satisfied only if user activity value B may not be classified as "perfect" for the user activity value type of the state's challenge type (e.g., as described with respect to state 1) and a second condition that may be satisfied only if user activity value B is not less than a threshold value φ (e.g., as described with respect to state 2) and a third condition that may be satisfied only if user activity level B is equal to user activity level A, and if each of those conditions is satisfied, then a challenge may be proposed by the state that challenges a user to generate a user activity value C that is equal to user activity value B plus 1. The satisfaction of these conditions of state 7 (e.g., no regression or improvement between time intervals TIA and TIB) may be indicative of a user accomplishment during time interval TIB that is not sufficient enough to warrant challenging a user merely to repeat the accomplishment, but warrants challenging the user to beat the achievement by an incremental amount.

State 8 of table 900 may include a first condition that may be satisfied only if user activity value B may not be classified as "perfect" for the user activity value type of the state's challenge type (e.g., as described with respect to state 1) and a second condition that may be satisfied only if user activity value B is not less than a threshold value φ (e.g., as described with respect to state 2) and a third condition that may be satisfied only if user activity level B is less than user activity level A and a fourth condition that may be satisfied only if user activity level B is not less than a threshold percentage λ of user activity level A, and if each of those conditions is satisfied, then a challenge may be proposed by the state that challenges a user to generate a user activity value C that is equal to an average of user activity values A and B. The value of such a threshold percentage λ may vary based on the user activity value type of the state's challenge type, but an achievement of user activity value B being within a percentage range of λ and 100% of user activity value A may be indicative of a user accomplishment during time interval TIB that fails to beat the user accomplishment during time interval TIA by a relative amount so as to warrant challenging a user to meet an average of the two accomplishments rather than merely repeat the regression accomplishment of time interval TIB. For example, threshold percentage λ may be 50% (e.g., such that value B is less than value A but no less than 50% of value A) or any other suitable percentage.

State 9 of table 900 may include a first condition that may be satisfied only if user activity value B may not be classified as "perfect" for the user activity value type of the state's challenge type (e.g., as described with respect to state 1) and a second condition that may be satisfied only if user activity value B is not less than a threshold value φ (e.g., as described with respect to state 2) and a third condition that may be satisfied only if user activity level B is less than a threshold percentage λ of user activity level A (e.g., as described with respect to state 8) and a fourth condition that may be satisfied only if user activity level B is greater than a threshold percentage ψ of user activity level A, and if each of those conditions is satisfied, then a challenge may be proposed by the state that challenges a user to generate a user activity value C that is equal to a threshold percentage ς of user activity value B. The value of such a threshold percentage λ and of such a threshold percentage ψ may vary based on the user activity value type of the state's challenge type, but an achievement of user activity value B being within a percentage range of λ and ψ of user activity value A may be indicative of a user accomplishment during time interval TIB that fails to beat the user accomplishment during time interval TIA by a relative amount so as to warrant challenging a user to meet a threshold percentage ç of user activity value B rather than merely repeating the regression accomplishment of time interval TIB. For example, threshold percentage λ may be 50% and threshold percentage ψ may be 0% (e.g., such that value B is less than 50% of value A but greater than 0% of value A) or any other suitable percentage.

State 10 of table 900 may include a first condition that may be satisfied only if user activity value B may not be classified as "perfect" for the user activity value type of the state's challenge type (e.g., as described with respect to state 1) and a second condition that may be satisfied only if user activity value B is not less than a threshold value φ (e.g., as described with respect to state 2) and a third condition that may be satisfied only if user activity level B is greater than a threshold percentage ω of the record (e.g., greatest) user activity value idefentified in any time interval prior to time interval TIB for the user activity value type of the state's challenge type, and if each of those conditions is satisfied, then a challenge may be proposed by the state that challenges a user to generate a user activity value C that is equal to that record user activity level plus 1 (or any other suitable value based on that record user activity level). The value of such a threshold percentage ω may vary based on the user activity value type of the state's challenge type, but an achievement of user activity value B being within a threshold percentage ω of the record activity user value may be indicative of a user accomplishment during time interval TIB that is sufficiently close to if not better than the record user activity level so as to warrant challenging a user to beat that accomplishment of time interval TIB (e.g., to motivate the user to try even harder than the significant achievement of the previous time interval). For example, threshold percentage ω may be 90% (e.g., such that value B is greater than 90% of the record value) or any other suitable percentage.

Different challenge types may be operative to identify a particular current state from different sets of two or more possible states (e.g., a first challenge type for a first user activity value type (e.g., activity value type (1) of the above-list) may use all 10 states of table 900, while a different challenge type for a different user activity value type (e.g., activity value type (11) of the above-list) may only use states 5-10 of table 900 and/or at least one other state not depicted by table 900). Additionally or alternatively, different challenge types may identify a particular current state using the same possible state, but the different challenge types may use different values for one or more thresholds associated with that possible state (e.g., a first challenge type and a second challenge type may each include possible state 3 of table 900, but the value of threshold φ of state 3 and/or the value of threshold α of state 3 may differ between the first challenge type and the second challenge type). In some embodiments, one or more challenge types may include one or more states similar to one or more states of table 900 but without one or more conditions (e.g., the first condition and/or the second condition of one or more of states 3-10 may not be included in similar states of certain challenge types (e.g., challenge types for user activity value types that are for total Calories burned or for average distance traveled per sub-interval, etc.). In some embodiments, user activity value A may be an average of two or more time intervals that occurred prior to time interval TIB rather than just being the user activity value of one time interval prior to time interval TIB. While certain examples may be described herein with respect to monthly time intervals and daily time sub-intervals, it is to be appreciated that any suitable time interval that includes two or more of any suitable time sub-interval may be used. For example, a time sub-interval may be a day, while the time interval may be a week or two weeks or a month or a season or a year. Alternatively, a time sub-interval may be a week and the time interval may be two weeks or a month or a season or a year. Alternatively, a time sub-interval may be an hour and the time interval may be a day or a week or two weeks or a month or a season or a year.

Any suitable number of challenge types may be made available for defining challenges based on particular detected user activity data. One, some, or each challenge type may be used to define a challenge for an upcoming time interval based on analysis of user activity data detected during one or more previous time intervals, and then one, some, or each defined challenge may be selected for use in challenging a user to achieve the challenge during the upcoming time interval. For example, in some embodiments, each one of two or more challenge types may be made available for use in potentially defining a challenge for an upcoming time interval based on user activity data detected during one or more previous time intervals (e.g., 15 challenge types (e.g., a challenge type for each of the above-listed 15 user activity value types), although, it is to be appreciated that some challenge types may not be applicable if certain types of user activity are not monitored (e.g., device 100 may or may not be configured to detect a number of Calories burned, and/or device 100 may or may not be configured to define a time sub-interval goal for distance traveled, and/or the like)). In some embodiments, for each challenge type of at least two available challenge types, first time interval user activity value A and second timer interval user activity value B may be identified for the user activity value type of that challenge type and may be compared with one another (e.g., using one or more states of that challenge type (e.g., evaluating the potential satisfaction of various conditions of various states of that challenge type)) to define a challenge for that challenge type (e.g., a challenge for the state of that challenge type whose conditions were all satisfied), and then the defined challenges for each of the at least two available challenge types may be analyzed (e.g., compared) to select at least one of those defined challenges as a user challenge for the upcoming time interval and/or to present to the user such that the user may select at least one of those defined challenges as a user challenge for the upcoming time interval (e.g., analysis may identify a first of those defined challenges as a "safe" or "easy" challenge and a second of those defined challenges as an "adventurous" or "difficult" challenge and may automatically select one of them based on pre-defined user settings or heuristics or may present both distinct options to a user (e.g., ordered from easiest to hardest or otherwise) such that the user may select one or both or neither of the challenges. In some embodiments, only a particular one or a particular subset of available challenge types may be used to define any challenge(s) that may be considered for use in the upcoming time interval (e.g., a challenge type that was used to define the challenge presented to the user in the previous time interval or any recent time interval may not be used as a candidate for defining the challenge for the upcoming time interval). In some embodiments, a first challenge type may be selected randomly or pseudo-randomly or randomly in combination with any suitable heuristics in order to use the selected challenge type to define a challenge that may be used for the upcoming time interval, yet if such a selected challenge type results in no challenge being defined (e.g., if only the condition of state 1 of table 900 is satisfied for the particular challenge type selected) then another challenge type may be selected. The history of previously presented and/or selected challenge types for one or more previous time intervals may be retained and used to affect determination of a new challenge type for an upcoming time interval. For example, in some embodiments, the system may be configured to prevent the same challenge type from being selected for use in two consecutive time intervals or perhaps even in two out of three or more consecutive time intervals so that variety amongst presented challenges may be ensured. Therefore, the content of one or more challenges may be customized to a user based on the achievements of that user during one or more previous time intervals, and the type of a challenge presented to one user may be different than a challenge type that may be presented to another user (e.g., due to randomness and/or due to the specific user's previous achievements). While one or more specific algorithms have been provided for defining a new challenge, it should be appreciated that other algorithms can be used to define new challenges in any suitable manner based on one or more previous achievements of the user and/or otherwise.

Device 100 may be configured to present one or more challenges to a user in any suitable manner at any suitable moment, such as during the first instance during a new time interval that a user interfaces with a fitness application of device 100 (e.g., along with a summary of the user's physical activity achievement(s) during the recently completed previous time interval) or otherwise. For example, as shown by GUI screen 190*a* of FIG. 2A, device 100 may be operative to present a new challenge for a new time interval while providing a summary of physical activity from the previous time interval (e.g., "YOUR NEW MONTHLY CHALLENGE—Congratulations John Doe! You achieved your daily goal for Calories Burned on 23 separate occasions last month (up from 20 occasions the month prior). Well done! To push yourself even further, achieve your daily goal for Calories Burned at least 28 days this month in order to get this award:" (e.g., a challenge of state 4 of table 900 for a challenge type associated with user activity value type (1) of the above list)) while optionally presenting a graphical representation of the reward to further motivate the user, where the user may accept the challenge, request automatic selection or manual user selection of one or more alternative or additional challenges (e.g., an easier or more difficult challenge), and/or review the status of one or more previous challenges. At any suitable sub-interval of the time interval associated with the challenge, device 100 may be configured to present any suitable status update with respect to the user's progress towards achieving the challenge for that time interval (e.g., at the end of each week of the month time interval). For example, as shown by GUI screen 190*b* of FIG. 2B, device 100 may be operative to present a challenge status update during the time interval (e.g., after the first two weeks of the month) while providing a summary of physical activity from the current time interval (e.g., "YOUR CURRENT MONTHLY CHALLENGE—(2 week status update)—Keep going John Doe! You achieved your daily goal for Calories Burned on 13 of the first 14 days of this month. You are on pace to accomplish this month's challenge and win this award:") while optionally presenting a graphical representation of the reward to further motivate the user (e.g., as may be visually updated to indicate the progress already made towards achieving the reward). Alternatively, if appropriate, a status update during the current time interval may indicate that the user is no longer able to achieve the challenge (e.g., if there are not enough days left in the month to satisfy a daily goal in order to satisfy a requirement of the challenge). Additionally or alternatively, if appropriate, a status update may be provided once a user achieves a challenge with any suitable congratulatory message and/or by adding a reward associated with the completed challenge to a rewards collection for the user (e.g., a virtual trophy shelf). For example, as shown by GUI screen 190*c* of FIG. 2C, device 100 may be operative to present a challenge status update during or at the end of the time interval while providing a summary of physical activity from the current time interval indicative of the achieved challenge (e.g., "YOUR CURRENT MONTHLY CHALLENGE—(Challenge Completed)—Congratulations John Doe! You have already achieved your daily goal for Calories Burned on 23 days this month! You have accomplished this month's challenge and have won this award:") while optionally presenting a graphical representation of the reward to further motivate or incentivize the user to continue interacting with such challenges in the future (e.g., as may be visually updated to indicate the achievement of the reward).

In response to a selection of a reward or badge (e.g., as may be associated with a new challenge, with a current challenge already progressing towards achievement, or with an achieved challenge), device 100 may be operative to display additional information associated with the reward, such as the date that the reward was obtained, information about the physical activity during which the reward was or is currently being obtained, or the like. In some examples, rewards obtained by the user can be displayed in color, while rewards not yet obtained by the user can be displayed as being grayed-out, while rewards currently being obtained can be displayed partially in color or partially shaded to indicate the progress. An aggregated view of all challenge rewards may be presented in response to selection of a review option of one or more of GUI screens 190*a*-190*c*. Examples of rewards include, but are not limited to, visual rewards, such as animations, glowing or pulsating graphics, three-dimensional images, lighting effects, badges, or the like; sound rewards, such as alerts, ringtones, music, voice, or the like; vibrations; or any combinations of rewards thereof.

Figure 5:
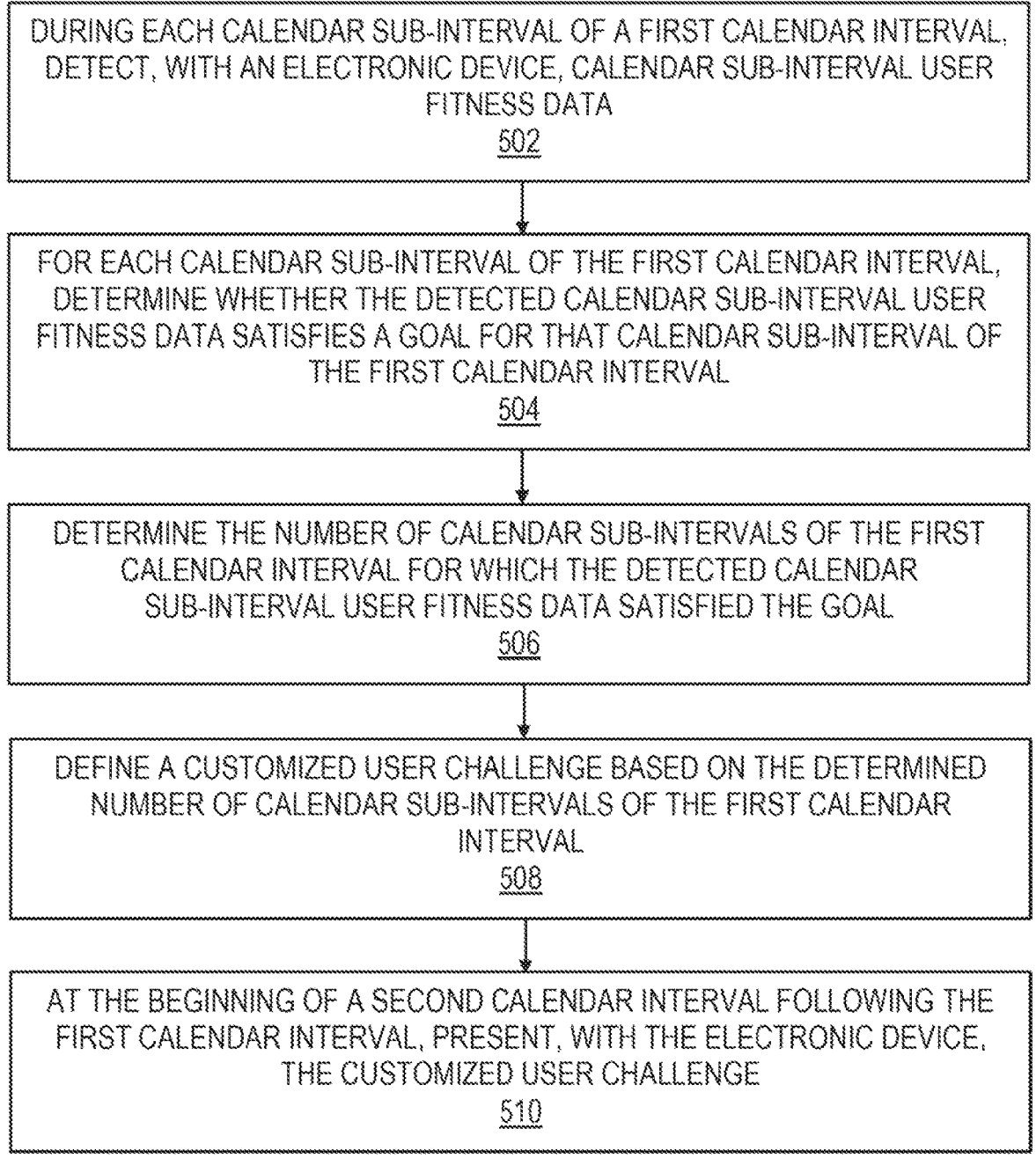
FIGS. 5-8 are flowcharts of illustrative processes for operating an electronic device for motivating a user.

FIG. 5 is a flowchart of an illustrative process 500 for operating an electronic device to motivate a user. At operation 502 of process 500, during each calendar sub-interval of a first calendar interval, calendar sub-interval user fitness data may be detected with the electronic device. At operation 504 of process 500, for each calendar sub-interval of the first calendar interval, whether the detected calendar sub-interval user fitness data satisfies a goal for that calendar sub-interval of the first calendar interval may be determined. At operation 506 of process 500, the number of calendar sub-intervals of the first calendar interval for which the detected calendar sub-interval user fitness data satisfied the goal may be determined. At operation 508 of process 500, a customized user challenge based on the determined number of calendar sub-intervals of the first calendar interval may be defined. At operation 510 of process 500, the customized user challenge may be presented with the electronic device at the beginning of a second calendar interval following the first calendar interval (e.g., a challenge for a second month may be customized and presented based on a determination of the number of days in a first month for which a Calories burned daily goal was satisfied).

It is understood that the operations shown in process 500 of FIG. 5 are only illustrative and that existing operations may be modified or omitted, additional operations may be added, and the order of certain operations may be altered.

Figure 6:
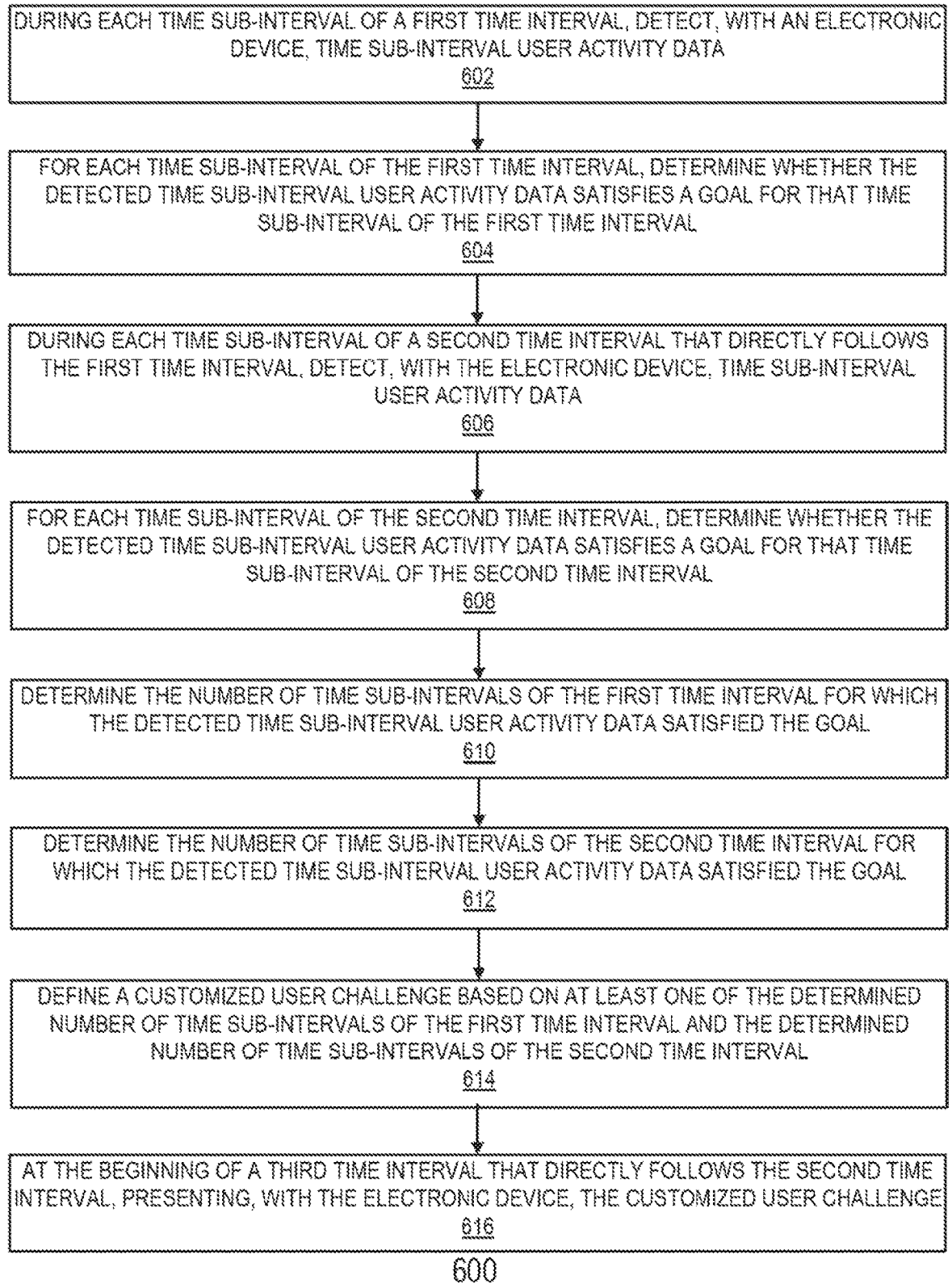

FIG. 6 is a flowchart of an illustrative process 600 for operating an electronic device to motivate a user. At operation 602 of process 600, during each time sub-interval of a first time interval, time sub-interval user activity data may be detected with the electronic device. At operation 604 of process 600, for each time sub-interval of the first time interval, whether the detected time sub-interval user activity data satisfies a goal for that time sub-interval of the first time interval may be determined. At operation 606 of process 600, during each time sub-interval of a second time interval that directly follows the first time interval, time sub-interval user activity data may be detected with the electronic device. At operation 608 of process 600, for each time sub-interval of the second time interval, whether the detected time sub-interval user activity data satisfies a goal for that time sub-interval of the second time interval may be determined. At operation 610 of process 600, the number of time sub-intervals of the first time interval for which the detected time sub-interval user activity data satisfied the goal may be determined. At operation 612 of process 600, the number of time sub-intervals of the second time interval for which the detected time sub-interval user activity data satisfied the goal may be determined. At operation 614 of process 600, a customized user challenge may be defined based on at least one of the determined number of time sub-intervals of the first time interval and the determined number of time sub-intervals of the second time interval. At operation 616 of process 600, the customized user challenge may be presented with the electronic device at the beginning of a third time interval that directly follows the second time interval (e.g., a challenge for a third month may be customized and presented based on a determination of the number of days in a first month for which a Calories burned daily goal was satisfied and based on a determination of the number of days in a second month for which a Calories burned daily goal was satisfied).

It is understood that the operations shown in process 600 of FIG. 6 are only illustrative and that existing operations may be modified or omitted, additional operations may be added, and the order of certain operations may be altered.

Figure 7:
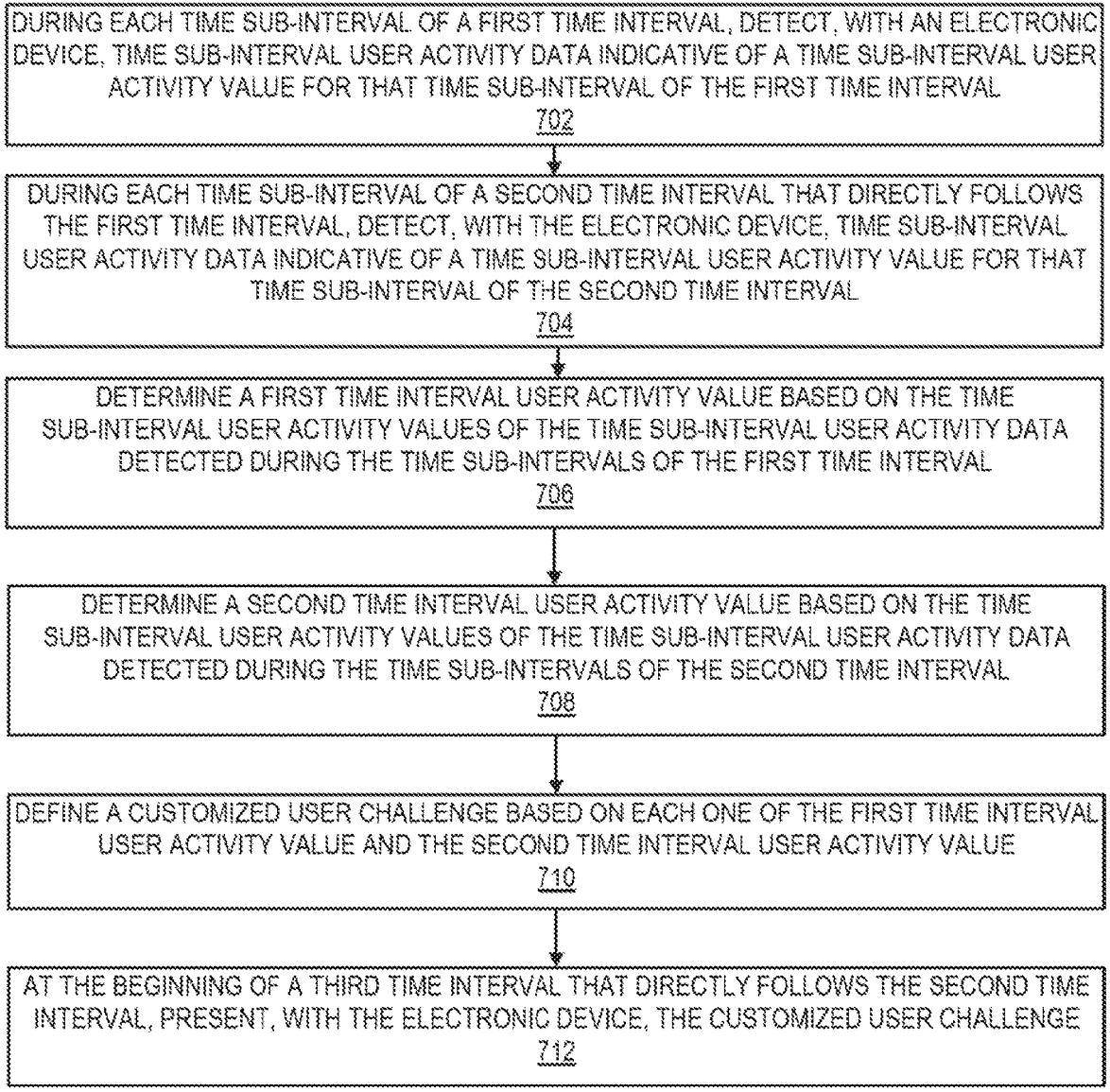

FIG. 7 is a flowchart of an illustrative process 700 for operating an electronic device to motivate a user. At operation 702 of process 700, during each time sub-interval of a first time interval, time sub-interval user activity data indicative of a time sub-interval user activity value for that time sub-interval of the first time interval may be detected with the electronic device. At operation 704 of process 700, during each time sub-interval of a second time interval that directly follows the first time interval, time sub-interval user activity data indicative of a time sub-interval user activity value for that time sub-interval of the second time interval may be detected with the electronic device. At operation 706 of process 700, a first time interval user activity value based on the time sub-interval user activity values of the time sub-interval user activity data detected during the time sub-intervals of the first time interval may be determined. At operation 708 of process 700, a second time interval user activity value based on the time sub-interval user activity values of the time sub-interval user activity data detected during the time sub-intervals of the second time interval may be determined. At operation 710 of process 700, a customized user challenge may be defined based on each one of the first time interval user activity value and the second time interval user activity value. At operation 712 of process 700, at the beginning of a third time interval that directly follows the second time interval, the customized user challenge may be presented with the electronic device (e.g., a challenge for a third month may be customized and presented based on a determination of the average Calories burned per day in a first month and based on a determination of the average Calories burned per day in a second month). In some embodiments of process 700, at least two of the following may be true: (i) when the second time interval user activity value is within a first range of threshold percentages of the first time interval user activity value, the defining comprises defining the customized user challenge to challenge the user to generate, during the third time interval, third time interval user activity data indicative of a third time interval user activity value that is equal to a first threshold percentage of the second time interval user activity value; (ii) when the second time interval user activity value is within a second range of threshold percentages of the first time interval user activity value, the defining comprises defining the customized user challenge to challenge the user to generate, during the third time interval, third time interval user activity data indicative of a third time interval user activity value that is equal to the whole number that is closest to a second threshold percentage of the second time interval user activity value; (iii) when the second time interval user activity value is within a third range of threshold percentages of the first time interval user activity value, the defining comprises defining the customized user challenge to challenge the user to generate, during the third time interval, third time interval user activity data indicative of a third time interval user activity value that is equal to the whole number that is closest to a third threshold percentage of the second time interval user activity value; (iv) when the second time interval user activity value is equal to the first time interval user activity value, the defining comprises defining the customized user challenge to challenge the user to generate, during the third time interval, third time interval user activity data indicative of a third time interval user activity value that is greater than the second time interval user activity value by 1; (v) when the second time interval user activity value is within a fourth range of threshold percentages of the first time interval user activity value, the defining comprises defining the customized user challenge to challenge the user to generate, during the third time interval, third time interval user activity data indicative of a third time interval user activity value that is equal to the whole number that is closest to the average of the first time interval user activity value and the second time interval user activity value; and (vi) when the second time interval user activity value is within a fifth range of threshold percentages of the first time interval user activity value, the defining comprises defining the customized user challenge to challenge the user to generate, during the third time interval, third time interval user activity data indicative of a third time interval user activity value that is equal to the whole number that is closest to the third threshold percentage of the second time interval user activity value. In such embodiments, the first range of threshold percentages of the first time interval user activity value is from 121% to 130%, the first threshold percentage of the second time interval user activity value is 100%, the second range of threshold percentages of the first time interval user activity value is from 111% to 120%, the second threshold percentage of the second time interval user activity value is 120%, the third range of threshold percentages of the first time interval user activity value is from 101% to 110%, the third threshold percentage of the second time interval user activity value is 110%, the fourth range of threshold percentages of the first time interval user activity value is from 50% to 99%, and/or the fifth range of threshold percentages of the first time interval user activity value is from 0% to 49%.

It is understood that the operations shown in process 700 of FIG. 7 are only illustrative and that existing operations may be modified or omitted, additional operations may be added, and the order of certain operations may be altered.

Figure 8:
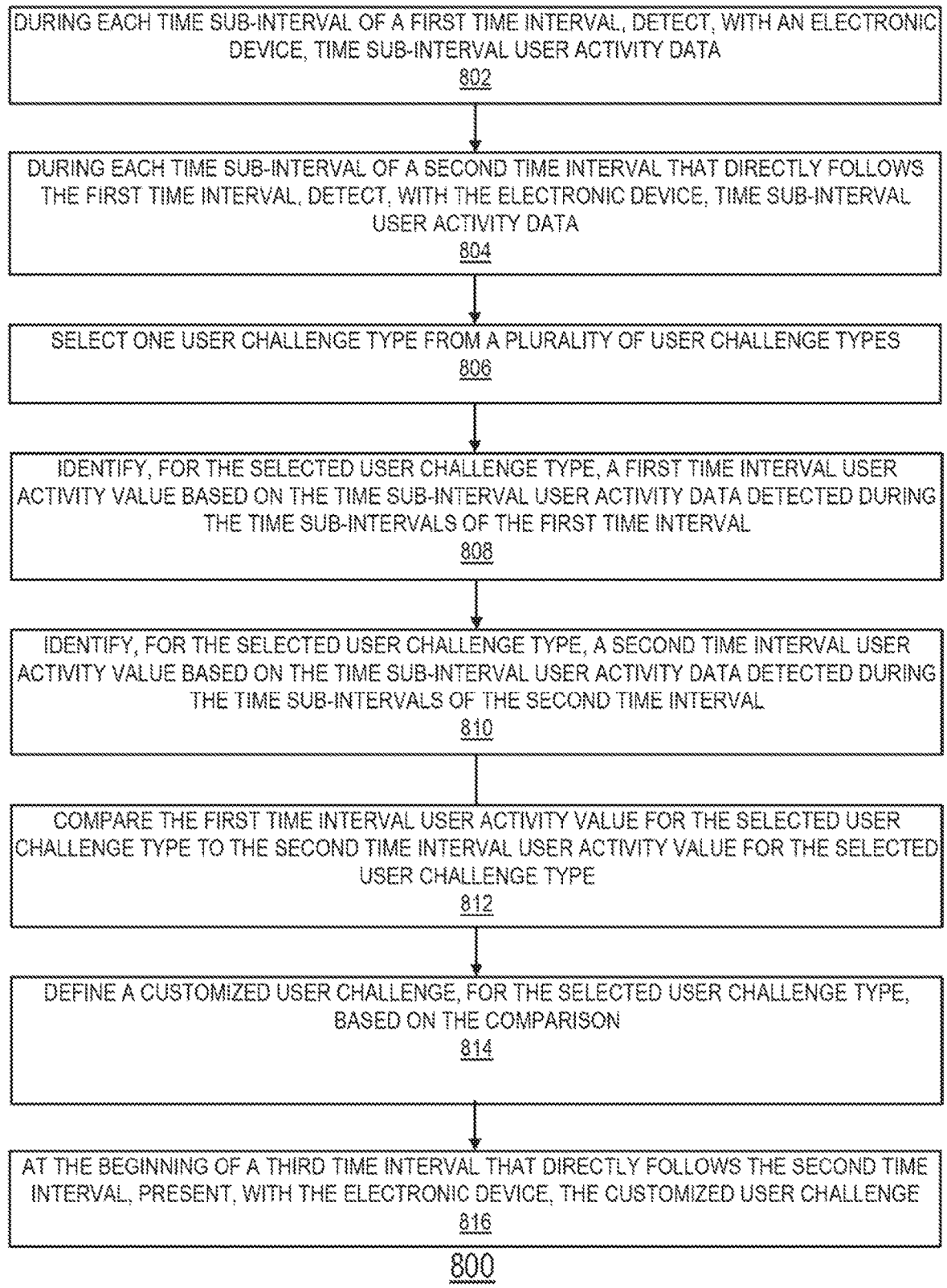

FIG. 8 is a flowchart of an illustrative process 800 for operating an electronic device to motivate a user. At operation 802 of process 800, during each time sub-interval of a first time interval, time sub-interval user activity data may be detected with the electronic device. At operation 804 of process 800, during each time sub-interval of a second time interval that directly follows the first time interval, time sub-interval user activity data may be detected with the electronic device. At operation 806 of process 800, one user challenge type may be selected from a plurality of user challenge types. At operation 808 of process 800, for the selected user challenge type, a first time interval user activity value may be identified based on the time sub-interval user activity data detected during the time sub-intervals of the first time interval. At operation 810 of process 800, for the selected user challenge type, a second time interval user activity value may be identified based on the time sub-interval user activity data detected during the time sub-intervals of the second time interval. At operation 812 of process 800, the first time interval user activity value for the selected user challenge type may be compared to the second time interval user activity value for the selected user challenge type. At operation 814 of process 800, a customized user challenge, for the selected user challenge type, may be defined based on the comparing. At operation 816 of process 800, at the beginning of a third time interval that directly follows the second time interval, the customized user challenge may be presented by the electronic device (e.g., a challenge type may be selected and user activity value B may be compared to user activity value A (e.g., using one or more conditions of one or more states of the challenge type) to define a customized user challenge for presentation).

It is understood that the operations shown in process 800 of FIG. 8 are only illustrative and that existing operations may be modified or omitted, additional operations may be added, and the order of certain operations may be altered.

Moreover, one, some, or all of the processes described with respect to FIGS. 1-9 may each be implemented by software, but may also be implemented in hardware, firmware, or any combination of software, hardware, and firmware. They each may also be embodied as machine- or computer-readable code recorded on a machine- or computer-readable medium. The computer-readable medium may be any data storage device that can store data or instructions which can thereafter be read by a computer system. Examples of such a non-transitory computer-readable medium (e.g., memory 104 of FIG. 1) may include, but are not limited to, read-only memory, random-access memory, flash memory, CD-ROMs, DVDs, magnetic tape, removable memory cards, optical data storage devices, and the like. The computer-readable medium can also be distributed over network-coupled computer systems so that the computer-readable code is stored and executed in a distributed fashion. For example, the computer-readable medium may be communicated from one electronic device to another electronic device using any suitable communications protocol (e.g., the computer-readable medium may be communicated to electronic device 100 via communications component 106 (e.g., as at least a portion of application 103)). Such a transitory computer-readable medium may embody computer-readable code, instructions, data structures, program modules, or other data in a modulated data signal, such as a carrier wave or other transport mechanism, and may include any information delivery media. A modulated data signal may be a signal that has one or more of its characteristics set or changed in such a manner as to encode information in the signal.

As described above, one aspect of the present technology is the gathering and use of data available from various sources to monitor and motivate physical activity with an electronic device. The present disclosure contemplates that in some instances, this gathered data may include personal information data that uniquely identifies or can be used to contact or locate a specific person. Such personal information data can include demographic data, location-based data, telephone numbers, email addresses, social network identifiers, home addresses, office addresses, data or records relating to a user's health or level of fitness (e.g., vital signs measurements, medication information, exercise information, etc.), date of birth, or any other identifying or personal information.

The present disclosure recognizes that the use of such personal information data, in the present technology, can be used to the benefit of users. For example, the personal information data can be used to improve the monitoring and/or motivating with the electronic device. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the United States, collection of or access to certain health data may be governed by federal and/or state laws, such as the Health Insurance Portability and Accountability Act ("HIPAA"); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of location detection services, the present technology can be configured to allow users to select to "opt in" or "opt out" of participation in the collection of personal information data during registration for services or anytime thereafter. In addition to providing "opt in" or "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, the determination of movement states of an electronic device can be made based on non-personal information data or a bare minimum amount of personal information, such as the content being requested by the device associated with a user, other non-personal information available to the device, or publicly available information.

While there have been described systems, methods, and computer-readable media for monitoring and motivating physical activity with an electronic device, it is to be understood that many changes may be made therein without departing from the spirit and scope of the subject matter described herein in any way. Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

Therefore, those skilled in the art will appreciate that the invention can be practiced by other than the described embodiments, which are presented for purposes of illustration rather than of limitation.

What is claimed is:

1. A method of operating an electronic device comprising sensor circuitry to motivate a user, the method comprising:
    during each time sub interval of a first time interval, detecting, at least partially with the sensor circuitry of the electronic device, time sub interval user activity data;
    for each time sub interval of the first time interval, determining whether the detected time sub interval user activity data satisfies a goal for that time sub interval of the first time interval;
    during each time sub interval of a second time interval that directly follows the first time interval, detecting, at least partially with the sensor circuitry of the electronic device, time sub interval user activity data;
    for each time sub interval of the second time interval, determining whether the detected time sub interval user activity data satisfies a goal for that time sub interval of the second time interval;
    determining the number of time sub intervals of the first time interval for which the detected time sub interval user activity data satisfied the goal;
    determining the number of time sub intervals of the second time interval for which the detected time sub interval user activity data satisfied the goal;
    comparing the determined number of time sub intervals of the first time interval to the determined number of time sub intervals of the second time interval;
    defining, with the electronic device, a customized user challenge based on the comparing, the customized user challenge corresponding to a first type of user activity data and including an activity goal that corresponds to the first type of user activity data and is achievable during at least one time interval subsequent to the second time interval;
    at the beginning of a third time interval that directly follows the second time interval, presenting, with the electronic device, a first view of a graphical user interface that identifies the customized user challenge and includes an option for accepting the customized user challenge;
    receiving, via a physical input component of the electronic device, a user input that selects the option for accepting the customized user challenge included in the first view of the graphical user interface;
    after receiving the user input, presenting, with the electronic device, a second view of the graphical user interface that includes a combined activity indicator comprising a plurality of graphic indicators, a first graphic indicator of the plurality of graphic indicators representing: (i) user activity data of the first type of user activity data received by the sensor circuitry of the electronic device, and (ii) user progress towards achieving a first portion of the activity goal based on the received user activity data of the first type of user activity data;
    receiving, by the sensor circuitry of the electronic device, updated user activity data of the first type of user activity data; and
    responsive to receiving the updated user activity data, updating in real-time the first graphic indicator of the plurality of graphic indicators of the combined activity indicator based at least in part on the updated user activity data.

2. The method of claim 1, wherein the goal for each time sub interval of each one of the first time interval and the second time interval comprises a goal amount of burned Calories.

3. The method of claim 1, wherein the goal for each time sub interval of each one of the first time interval and the second time interval comprises a goal amount of time of exercise.

4. The method of claim 1, wherein the goal for each time sub interval of each one of the first time interval and the second time interval comprises a goal amount of distance traveled.

5. The method of claim 1, wherein the goal for each time sub interval of each one of the first time interval and the second time interval comprises a goal amount of workouts completed.

6. The method of claim 1, further comprising determining that the determined number of time sub intervals of the second time interval is at least a threshold percentage of the total number of time sub intervals of the second time interval, wherein:
   in response to the determining that the determined number of time sub intervals of the second time interval is at least the threshold percentage of the total number of time sub intervals of the second time interval, the defining the customized user challenge does not comprise challenging the user to generate, for any number of time sub intervals of the third time interval, user activity data that satisfies a particular type of goal for that time sub interval of the third time interval;
   the goal for each time sub interval of each one of the first time interval and the second time interval comprises one of a goal amount of burned Calories, a goal amount of time of exercise, and a goal amount of distance traveled; and
   the particular type of goal comprises the one of a goal amount of burned Calories, a goal amount of time of exercise, and a goal amount of distance traveled.

7. The method of claim 1, further comprising determining that the determined number of time sub intervals of the second time interval is less than a threshold number of time sub intervals, wherein:
   in response to the determining that the determined number of time sub intervals of the second time interval is less than the threshold number of time sub intervals, the defining the customized user challenge comprises defining the customized user challenge to challenge the user to generate, for each one of at least a challenge number of time sub intervals of the third time interval, user activity data that satisfies a goal for that time sub interval of the third time interval; and
   the challenge number of time sub intervals of the third time interval is greater than the determined number of time sub intervals of the second time interval by a time sub interval.

8. The method of claim 1, further comprising determining that the determined number of time sub intervals of the second time interval is not less than a threshold number of time sub intervals, wherein:
   in response to the determining that the determined number of time sub intervals of the second time interval is not less than the threshold number of time sub intervals: the comparing comprises determining that the determined number of time sub intervals of the second time interval is greater than a threshold percentage of the determined number of time sub intervals of the first time interval; and
   the defining the customized user challenge comprises defining the customized user challenge to challenge the user to generate, for each one of at least a challenge number of time sub intervals of the third time interval, user activity data that satisfies a goal for that time sub interval of the third time interval; and
   the challenge number of time sub intervals of the third time interval is equal to the determined number of time sub intervals of the second time interval.

9. The method of claim 1, further comprising determining that the determined number of time sub intervals of the second time interval is not less than a threshold number of time sub intervals, wherein:
   in response to the determining that the determined number of time sub intervals of the second time interval is not less than the threshold number of time sub intervals:
   the comparing comprises determining that the determined number of time sub intervals of the second time interval is within a range of threshold percentages of the determined number of time sub intervals of the first time interval; and
   the defining the customized user challenge comprises defining the customized user challenge to challenge the user to generate, for each one of at least a challenge number of time sub intervals of the third time interval, user activity data that satisfies a goal for that time sub interval of the third time interval; and
   the challenge number of time sub intervals of the third time interval is equal to the whole number that is closest to a threshold percentage of the determined number of time sub intervals of the second time interval.

10. The method of claim 1, further comprising determining that the determined number of time sub intervals of the second time interval is not less than a threshold number of time sub intervals, wherein:
    in response to the determining that the determined number of time sub intervals of the second time interval is not less than the threshold number of time sub intervals:
    the comparing comprises determining that the determined number of time sub intervals of the second time interval is equal to the determined number of time sub intervals of the first time interval; and
    the defining the customized user challenge comprises defining the customized user challenge to challenge the user to generate, for each one of at least a challenge number of time sub intervals of the third time interval, user activity data that satisfies a goal for that time sub interval of the third time interval; and
    the challenge number of time sub intervals of the third time interval is greater than the determined number of time sub intervals of the second time interval by a time sub interval.

11. The method of claim 1, further comprising determining that the determined number of time sub intervals of the second time interval is not less than a threshold number of time sub intervals, wherein:
    the comparing comprises comparing the determined number of time sub intervals of the first time interval to the determined number of time sub intervals of the second time interval in response to the determining that the determined number of time sub intervals of the second time interval is not less than the threshold number of time sub intervals;
    the comparing further comprises determining that the determined number of time sub intervals of the second time interval is less than the determined number of time sub intervals of the first time interval;

the defining comprises defining the customized user challenge to challenge the user to generate, for each one of at least a challenge number of time sub intervals of the third time interval, user activity data that satisfies a goal for that time sub interval of the third time interval; and
the challenge number of time sub intervals of the third time interval is equal to the determined number of time sub intervals of the second time interval.

12. The method of claim 1, further comprising determining that the determined number of time sub intervals of the second time interval is not less than a threshold number of time sub intervals, wherein:
the comparing comprises comparing the determined number of time sub intervals of the second time interval to a greatest number of time sub intervals of any time interval prior to the second time interval during which time sub interval user activity data was detected that satisfied a goal for each one of that greatest number of time sub intervals in response to the determining that the determined number of time sub intervals of the second time interval is not less than the threshold number of time sub intervals;
the comparing further comprises determining that the determined number of time sub intervals of the second time interval is greater than a threshold percentage of the greatest number of time sub intervals;
the defining comprises defining the customized user challenge to challenge the user to generate, for each one of at least a challenge number of time sub intervals of the third time interval, user activity data that satisfies a goal for that time sub interval of the third time interval; and
the challenge number of time sub intervals of the third time interval is greater than the greatest number of time sub intervals by one time sub interval.

13. The method of claim 1, wherein:
for each time sub interval of the first time interval, the determining further comprises determining whether the detected time sub interval user activity data doubly satisfies the goal for that time sub interval of the first time interval;
for each time sub interval of the second time interval, the determining further comprises determining whether the detected time sub interval user activity data doubly satisfies the goal for that time sub interval of the second time interval;
the method further comprising:
determining another other number of time sub intervals of the first time interval for which the detected time sub interval user activity data doubly satisfied the goal; and
determining another other number of time sub intervals of the second time interval for which the detected time sub interval user activity data doubly satisfied the goal; and
the defining further comprises defining the customized user challenge based on at least one of:
the determined other number of time sub intervals of the first time interval; or
the determined other number of time sub intervals of the second time interval.

14. A wearable electronic device, comprising:
sensor circuitry configured to sense physical activity of a wearer of the wearable electronic device;
an output component configured to generate a graphical user interface;
a physical input component;
a memory configured to store computer-executable instructions;
a processor configured to access the memory and execute the computer-executable instructions to at least:
during each time sub interval of a first time interval, detect time sub interval user activity data;
for each time sub interval of the first time interval, determine whether the detected time sub interval user activity data satisfies a goal for that time sub interval of the first time interval;
during each time sub interval of a second time interval that directly follows the first time interval, detect time sub interval user activity data;
for each time sub interval of the second time interval, determine whether the detected time sub interval user activity data satisfies a goal for that time sub interval of the second time interval;
determine the number of time sub intervals of the first time interval for which the detected time sub interval user activity data satisfied the goal;
determine the number of time sub intervals of the second time interval for which the detected time sub interval user activity data satisfied the goal;
compare the determined number of time sub intervals of the first time interval to the determined number of time sub intervals of the second time interval;
define a customized user challenge based on the comparing, the customized user challenge corresponding to a first type of user activity data and including an activity goal that corresponds to the first type of user activity data and is achievable during at least one time interval subsequent to the second time interval;
at the beginning of a third time interval that directly follows the second time interval, present, using the output component, a first view of a graphical user interface that identifies the customized user challenge and includes an option for accepting the customized user challenge;
receive, via the physical input component, a user input that selects the option for accepting the customized user challenge included in the first view of the graphical user interface;
after receiving the user input, present, using the output component, a second view of the graphical user interface that includes a combined activity indicator comprising a plurality of graphic indicators, a first graphic indicator of the plurality of graphic indicators representing: (i) user activity data of the first type of user activity data received by the sensor circuitry of the wearable electronic device, and (ii) user progress towards achieving a first portion of the activity goal based on the received user activity data of the first type of user activity data;
receive, by the sensor circuitry, updated user activity data of the first type of user activity data; and
responsive to receiving the updated user activity data, update in real-time the first graphic indicator of the plurality of graphic indicators of the combined activity indicator based at least in part on the updated user activity data.

15. The wearable electronic device of claim 14, wherein the plurality of graphic indicators comprise a plurality of rings.

16. The wearable electronic device of claim 15, wherein the plurality of rings are concentrically arranged.

17. The wearable electronic device of claim 14, wherein the activity goal is achievable during a time period comprising a plurality of sub-periods and the first portion of the activity goal is achievable during a first sub-period of the plurality of sub-periods.

18. One or more non-transitory computer-readable media comprising computer-executable instructions that, when executed by one or more processors of an electronic device, cause the electronic device to perform operations, comprising:

during each time sub interval of a first time interval, detecting, at least partially with sensor circuitry of the electronic device, time sub interval user activity data;

for each time sub interval of the first time interval, determining whether the detected time sub interval user activity data satisfies a goal for that time sub interval of the first time interval;

during each time sub interval of a second time interval that directly follows the first time interval, detecting, at least partially with the sensor circuitry of the electronic device, time sub interval user activity data;

for each time sub interval of the second time interval, determining whether the detected time sub interval user activity data satisfies a goal for that time sub interval of the second time interval;

determining the number of time sub intervals of the first time interval for which the detected time sub interval user activity data satisfied the goal;

determining the number of time sub intervals of the second time interval for which the detected time sub interval user activity data satisfied the goal;

comparing the determined number of time sub intervals of the first time interval to the determined number of time sub intervals of the second time interval;

defining, with the electronic device, a customized user challenge based on the comparing, the customized user challenge corresponding to a first type of user activity data and including an activity goal that corresponds to the first type of user activity data and is achievable during at least one time interval subsequent to the second time interval;

at the beginning of a third time interval that directly follows the second time interval, presenting, with the electronic device, a first view of a graphical user interface that identifies the customized user challenge and includes an option for accepting the customized user challenge;

receiving, via a physical input component of the electronic device, a user input that selects the option for accepting the customized user challenge included in the first view of the graphical user interface;

after receiving the user input, presenting, with the electronic device, a second view of the graphical user interface that includes a combined activity indicator comprising a plurality of graphic indicators, a first graphic indicator of the plurality of graphic indicators representing: (i) user activity data of the first type of user activity data received by the sensor circuitry of the electronic device, and (ii) user progress towards achieving a first portion of the activity goal based on the received user activity data of the first type of user activity data;

receiving, by the sensor circuitry of the electronic device, updated user activity data of the first type of user activity data; and responsive to receiving the updated user activity data, updating in real-time the first graphic indicator of the plurality of graphic indicators of the combined activity indicator based at least in part on the updated user activity data.

19. The one or more non-transitory computer-readable media of claim 18, wherein the goal for each time sub interval of each one of the first time interval and the second time interval comprises a goal amount of burned Calories.

20. The one or more non-transitory computer-readable media of claim 18, wherein the goal for each time sub interval of each one of the first time interval and the second time interval comprises a goal amount of time of exercise.

21. The one or more non-transitory computer-readable media of claim 18, wherein the goal for each time sub interval of each one of the first time interval and the second time interval comprises a goal amount of distance traveled.

* * * * *

UNITED STATES PATENT AND TRADEMARK OFFICE
CERTIFICATE OF CORRECTION

| | |
|---|---|
| PATENT NO. | : 11,224,782 B2 |
| APPLICATION NO. | : 15/888728 |
| DATED | : January 18, 2022 |
| INVENTOR(S) | : Jay K. Blahnik et al. |

It is certified that error appears in the above-identified patent and that said Letters Patent is hereby corrected as shown below:

In the Claims

Column 45, Claim 13, Line 47: please delete the word "another".

Column 45, Claim 13, Line 51: please delete the word "another".

Signed and Sealed this
Twenty-sixth Day of July, 2022

Katherine Kelly Vidal
*Director of the United States Patent and Trademark Office*